US008268581B2

(12) United States Patent (10) Patent No.: US 8,268,581 B2
Fox et al. (45) Date of Patent: Sep. 18, 2012

(54) CARBOXY TERMINAL RESIDUES AS PREDICTORS AND REGULATORS OF PROTEIN STABILITY

(75) Inventors: Brian G. Fox, Madison, WI (US); Yong Chang, Madison, WI (US); Gary A. Wesenberg, Madison, WI (US); Craig A. Bingman, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 508 days.

(21) Appl. No.: 12/431,315

(22) Filed: Apr. 28, 2009

(65) Prior Publication Data

US 2012/0107904 A1 May 3, 2012

Related U.S. Application Data

(60) Provisional application No. 61/049,255, filed on Apr. 30, 2008.

(51) Int. Cl.
*C12P 21/06* (2006.01)
*C07K 14/00* (2006.01)
*C07H 21/04* (2006.01)

(52) U.S. Cl. .................. 435/68.1; 435/69.1; 435/252.3; 435/253.1; 530/350

(58) Field of Classification Search .................. 530/350; 435/69.1, 69.7, 252.3, 253.1, 68.1
See application file for complete search history.

(56) References Cited

U.S. PATENT DOCUMENTS 5,290,690 A 3/1994 Mrabet et al.

OTHER PUBLICATIONS

Ishii et al., Biochemical Journal 358, 473-480 (2001).*
*Advanced Organic Chemistry: Reactions, Mechanisms and Structure*, 4th Ed., Wiley-Interscience, Interscience, New York, NY (1992).
Ausubel et al., *Current Protocols in Molecular Biology*, vols. 1-3, John Wiley & Sons, Inc., Hoboken, NJ (1993).
Blokpoel et al., "Development and Application of Unstable GFP Variants to Kinetic Studies of Mycobacterial Gene Expression," *J. Microbiol. Methods*, 54:203-211 (2003).
Blokpoel et al., "Tetracycline-inducible Gene Regulation in Mycobacteria," *Nucleic Acids Res.*, 33(2):e22, pp. 1-7 (2005).
Chang and Fox, "Identification of Rv3230c as the NADPH Oxidoreductase of a Two-Protein DesA3 Acyl-CoA Desaturase in *Mycobacterium tuberculosis* H37Rv," *Biochemistry*, 45:13476-13486 (2006).
Chang, et al., "In Vivo Inactivation of the Mycobacterial Integral Membrane Stearoyl Coenzyme A Desaturase DesA3 by a C-Terminus-Specific Degradation Process," *J. Bacteriol.*, 190:6686-6694 (2008).
Dye et al., "Global Burden of Tuberculosis," *JAMA*, 282(7):677-686 (1999).

Ehrt et al., "Controlling Gene Expression in Mycobacteria with Anhydrotetracycline and Tet Repressor," *Nucleic Acids Res.*, 33(2):e21, pp. 1-11 (2005).
Gottesman et al., "The ClpXP and ClpAP Proteases Degrade Proteins with Carboxy-terminal Peptide Tails Added by the SsrA-Tagging?System," *Genes Dev.*, 12:1338-1347 (1998).
Herman et al., Degradation of Carboxy-Terminal-Tagged Cytoplasmic Proteins by the *Escherichia coli* Protease HflB (FtsH), *Genes Dev.*, 12:1348-1355 (1998).
Hinz et al., "Fundamentals of Protein Stability," *Pure and Appl. Chem.*, 65(5)947-952 (1993).
Jackson et al., "Phosphatidylinositol Is an Essential Phospholipid of Mycobacteria," *J. Biol. Chem.*, 275(39):30092-30099 (2000).
Kato et al., "Ubiquitin-Proteasome-Dependent Degradation of Mammalian ER Stearroyl-CoA Desaturase," *J. Cell Sci.*, 119:2342-2353 (2006).
Keiler and Sauer, "Sequence Determinants of C-Terminal Substrate Recognition by the Tsp Protease," *J. Biol. Chem.*, 271(5):2589-2593 (1996).
Kim et al., "Dynamics of Substrate Denaturation and Translocation by the ClpXP Degradation Machine," *Mol. Cell.*, 5:639-648 (2000).
Kriegler, *Gene Transfer and Expression: A Laboratory Manual*, Stockton Press, New York, NY (1990).
Miyaji et al., "Expression of Human Lymphotoxin Derivatives in *Escherichia coli* and Comparison of Their Biological Activity In Vitro," *Agric. Biol. Chem.*, 53(1):277-279 (1989).
Mziaut et al., "The N Terminus of Microsomal Δ9 Stearoyl-CoA Desaturase Contains the Sequence Determinant for its Rapid Degradation," *Proc. Natl. Acad. Sci. USA*, 97(16):8883-8888 (2000).
Overman, *Organic Reactions*, John Wiley & Sons, Inc., Hoboken, NJ, vol. 66 (2005).
Parish et al., "Regulation of the Inducible Acetamidase Gene of *Mycobacterium smegmatis*," *Microbiology*, 143:2267-2276 (1997).
Pereira et al., "Identification of Residues Critical for Regulation of Protein Stability and the Transactivation Function of the Hypoxia-inducible Factor-1α by the von Hippel-Lindau Tumor Suppressor Gene Product," *J. Biol. Chem.*, 278(9):6816-6823 (2003).
Sambrook et al., *Molecular Cloning—A Laboratory Manual*, Cold Spring Harbor Laboratory, Cold Spring Harbor, New York, NY (1989).
Sassetti and Rubin, "Genetic Requirements for Mycobacterial Survival During Infection," *Proc. Natl. Acad. Sci. USA*, 100(22):12989-12994 (2003).

(Continued)

*Primary Examiner* — Chih-Min Kam
(74) *Attorney, Agent, or Firm* — Quarles & Brady LLP

(57) ABSTRACT

Compositions and methods are provided that are useful for predicting and controlling the stability of expressed polypeptides. The compositions and methods may be used to predict and as desired, increase or decrease the stability of proteins recombinantly expressed in mycobacteria, for example DesA3 expressed in *Mycobacterium smegmatis*. At the C terminus and the penultimate position, substitution to residues with charged side chains, large non-polar side chains, or no side chains can be used to reduce or inhibit the protein degradation. At the antepenultimate position from the C terminus, residues with no side chain or acidic side chains can increase the stability, i.e. reduce or inhibit the protein degradation. The combinational substitution of only the last three residues of polypeptides can make the polypeptides more stable during heterologous expression in mycobacterial hosts.

3 Claims, 8 Drawing Sheets

OTHER PUBLICATIONS

Scholz et al., Quantitative Analysis of Gene Expression with an Improved Green Fluorescent Protein, *Eur. J. Biochem.*, 267:1565-1570 (2000).

Sekine et al., loning and Expression of Cdna FOR Salmon Growth Hormone in *Escherichia coli*, *Proc. Natl. Acad. Sci. USA.*, 82: 4306-4310 (1985).

Snapper et al., "Isolation and Characterization of Efficient Plasmid Transformation Mutants of *Mycobacterium smegmatis*," *Mol. Microbiol.*, 4(11):1911-1919 (1990).

Yanisch-Perron et al., Improved M13 Phage Cloning Vectors and Host Strains: Nucleotide Sequences of the M13mp18 and pUC19 Vectors, *Gene*, 33:103-119 (1985).

* cited by examiner

FIGURE 1
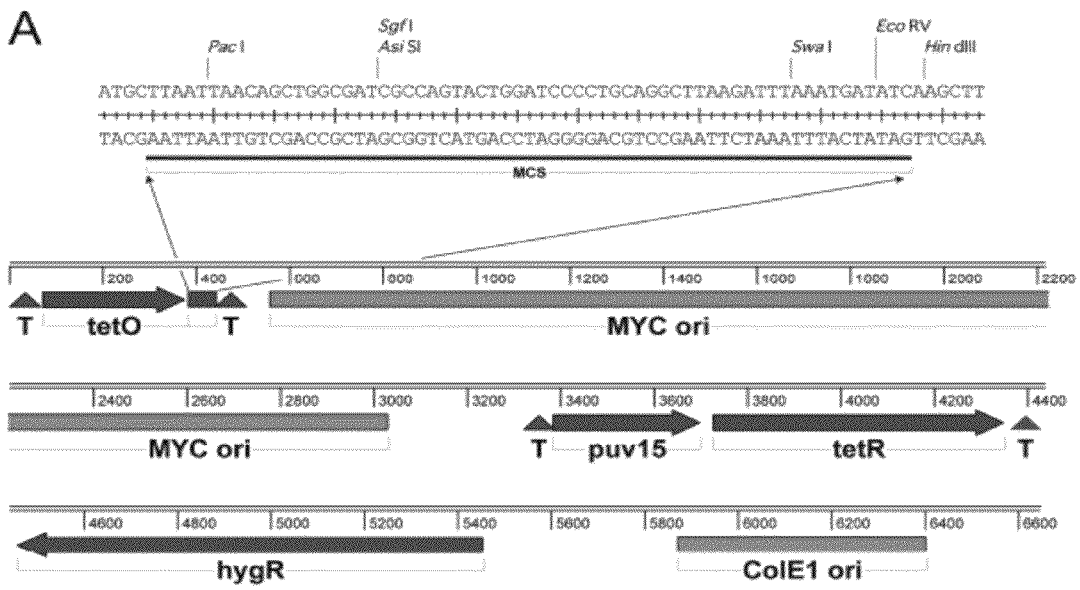
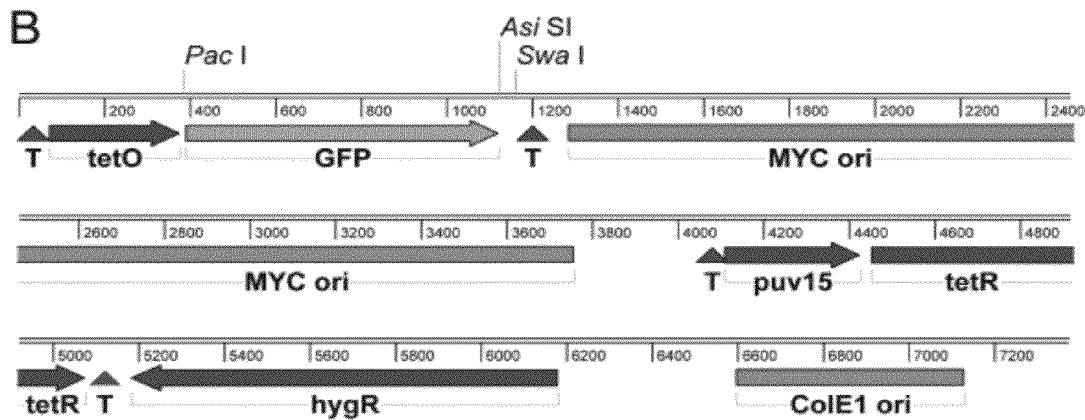

FIGURE 5
A. Position 1: DDLAX
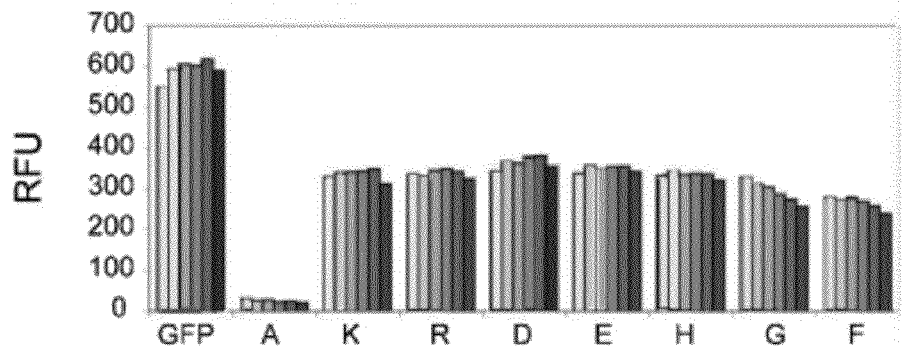
B. Position 2: DDLXA
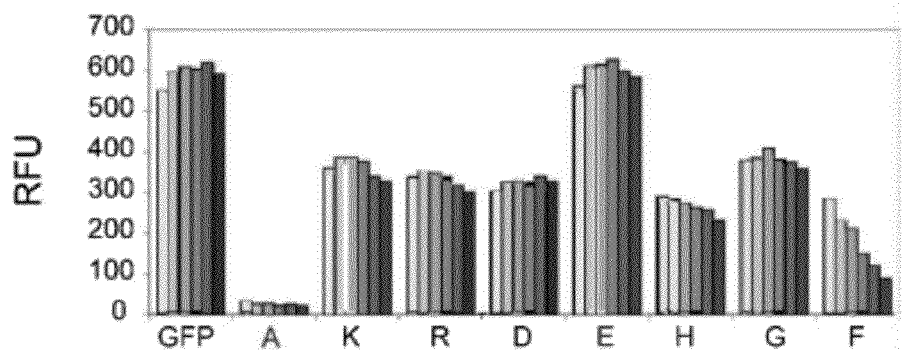
C. Position 3: DDXAA
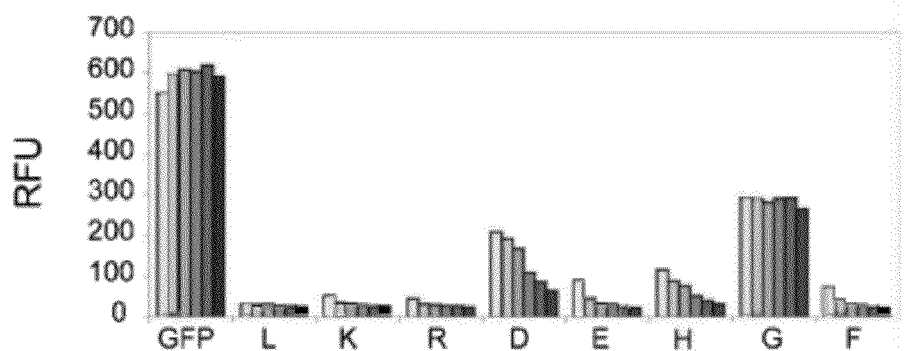
D. Positions 4 and 5: XXLAA
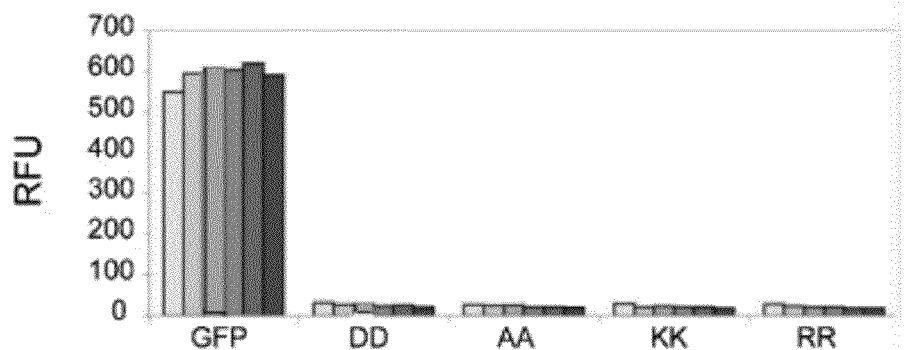

US 8,268,581 B2

CARBOXY TERMINAL RESIDUES AS PREDICTORS AND REGULATORS OF PROTEIN STABILITY

CROSS-REFERENCE TO RELATED APPLICATIONS

This invention claims priority to U.S. Provisional Patent Application Ser. No. 61/049,255, filed Apr. 30, 2008, which is herein incorporated by reference.

STATEMENT REGARDING FEDERALLY SPONSORED RESEARCH

This invention was made with government support under GM050853 awarded by the National Institutes of Health. The government has certain rights in the invention.

COMPUTER PROGRAM LISTING APPENDIX

This application hereby incorporates by reference the computer program listing appendix submitted on duplicate compact discs, each containing a file titled "python," having a size of 9.1 kilobytes and created on Jul. 11, 2012, and a file titled "output," having a size of 11.4 kilobytes and created on Jul. 11, 2012. The "python" file contains the computer program listing referenced in footnote 4 of Table 5. The "output" file contains the computer-generated output used to assemble Table 5.

FIELD OF THE INVENTION

This invention is related to the biomedical arts and provides compositions and methods for the prediction and regulation of protein stability.

BACKGROUND

*Mycobacterium tuberculosis* is a human pathogen that causes tuberculosis, one of the world's deadliest diseases. Current estimates are that up to one-third of the world's population may be infected with *M. tuberculosis*; over two million people die from TB-related diseases each year (Dye et al., 1999, *JAMA* 282: 677-686). Tuberculosis has resurged today, in part due to the lack of compliance to drug treatment regimes, the appearance of multiple-drug-resistant strains, and the AIDS epidemic. Consequently, increasing our understanding of the origins of pathogenicity of *M. tuberculosis* is a high priority of tuberculosis research.

In *Mycobacterium tuberculosis*, the desaturase DesA3 (encoded by gene rv3229c) is a membrane-bound stearoyl-CoA desaturase that works together with oxidoreductase Rv3230c (encoded by gene rv3230c) to produce oleic acid, an essential constituent of mycobacterial membrane phospholipids and triglycerides. Due to the physiological importance of oleic acid to bacteria, DesA3 is among the approximately 200 genes required for pathogen survival inside the granuloma enclosing a dormant tuberculosis infection. DesA3 is a target of the second-line anti-tuberculosis drug isoxyl, which has been used with isoniazid in multiple drug therapy.

To study mycobacterial pathogenicity, *Mycobacterium smegmatis* (*M. smegmatis*), a non-pathogenic strain that grows relatively faster than pathogenic mycobacteria and that transforms efficiently, has been widely used as a host for expression of target genes and proteins from pathogenic mycobacteria (Snapper et al., 1990, *Mol. Microbiol.* 4: 1911-1919). Many genes from pathogenic mycobacteria yield folded proteins and active enzymes when expressed in *M. smegmatis*, whereas the same genes expressed in *Escherichia coli* are neither folded nor active. The origin of this difference is not known. Currently, several different types of vectors have been developed for constitutive or inducible expression in *M. smegmatis* in order to access this biological capability (Blokpoel et al., 2005, *Nucleic Acids Res.* 33:e22; Ehrt et al., 2005, *Nucleic Acids Res.* 33: e21).

The inventors discovered that *M. tuberculosis* DesA3 expressed in *M. smegmatis* as a fusion with either a C-terminal His6 or a myc tag has higher catalytic activity and stability than DesA3 expressed with the natural C-terminal sequence (Chang and Fox, 2006, *Biochemistry* 45: 13476-13486). However, the origin of this difference was not known.

Within living cells, proteolysis is a ubiquitous and often selective process. In yeast and higher eukaryotes, some proteins are marked for degradation by modification with ubiquitin and targeted to the proteosome, and other specific routes for protein processing have been identified. Interestingly, proteolytic processing is also used to control mammalian desaturase activity (Kato et al., 2006, *J. Cell Sci.* 119: 2342-2353; Mziaut et al., 2000, *Proc. Natl. Acad. Sci. USA* 97: 8883-8888), although the proteolysis complexes used and the recognition sequences are distinct. This common approach to maintaining control of stearoyl-CoA desaturase activity serves to emphasize the importance of this key branch point in fatty acid metabolism.

Previous studies of the *E. coli* C-terminal targeted protein degradation systems ClpXP and Tsp showed that small and uncharged residues (Ala, Cys, Ser, Thr, Val) in last three positions of a protein enhanced the degradation (Kato et al., 2006, *J. Cell Sci.* 119: 2342-2353; Keiler and Sauer, 1996, *J. Biol. Chem.* 271: 2589-2593). In *E. coli* and other bacteria, several types of C-terminal targeted protein degradation complexes have been identified, including the ClpXP, ClpAP, FtsH (HflB), and Tsp (Prc) systems as major contributors to protein degradation in *E. coli* (Gottesman et al., 1998, *Genes Dev.* 1338-1347; Herman et al., 1998, *Genes Dev.* 12: 1348-1355; Keiler and Sauer, 1996, *J. Biol. Chem.* 271: 2589-2593). Among these, the Clp proteases are cytoplasmic, FtsH is a membrane protease, and Tsp is a periplasmic protease, ensuring that tagged proteins can be degraded in all cellular compartments. Thus the known proteolytic systems have different substrate recognition properties, and different contributions to proteolytic processing.

BRIEF SUMMARY

Non-naturally occurring polypeptides with amino acid sequences at least 99% homologous to naturally occurring polypeptide are provided, where the last three amino acid residues of the non-naturally occurring polypeptides are different from the last three amino acid residues of the naturally occurring polypeptides and where the non-naturally occurring polypeptides are more stable to proteolytic degradation compared to the naturally occurring polypeptides. The non-naturally occurring polypeptides may have at least one of the last three amino acid residues altered by amino acid substitution, amino acid insertion, or amino acid deletion. In some examples, at least one of the last two amino acid residues may be altered by amino acid substitution, amino acid insertion, or amino acid deletion. In some examples, one or both of the last two amino acid residues may be selected from the group consisting of Arg, Asp, Glu, Gly, His, Lys, Phe, Pro, Trp, and Tyr, and the antepenultimate amino acid residue may be selected from the group consisting of Asp, Gly, Glu, and His. In the non-naturally occurring polypeptides, the last three amino acid residues may have the sequence Asp-Lys-Asp, Leu-Glu-Ala, Leu-Lys-Ala, or Leu-Ala-Asp.

Polynucleotides are provided, which encode non-naturally occurring polypeptides with amino acid sequences at least 99% homologous to naturally occurring polypeptides, where the last three amino acid residues of the non-naturally occurring polypeptides are different from the last three amino acid residues of the naturally occurring polypeptides and where the non-naturally occurring polypeptides are more stable to proteolytic degradation compared to the naturally occurring polypeptides. The polynucleotides may encode non-naturally occurring polypeptides that have at least one of the last three amino acid residues altered by amino acid substitution, amino acid insertion, or amino acid deletion. In some examples, at least one of the last two amino acid residues may be altered by amino acid substitution, amino acid insertion, or amino acid deletion. In some examples, one or both of the last two amino acid residues may be selected from the group consisting of Arg, Asp, Glu, Gly, His, Lys, Phe, Pro, Trp, and Tyr, and the antepenultimate amino acid residue may be selected from the group consisting of Asp, Gly, Glu, and His. In the non-naturally occurring polypeptides encoded by the polynucleotides, the last three amino acid residues may have the sequence Asp-Lys-Asp, Leu-Glu-Ala, Leu-Lys-Ala, or Leu-Ala-Asp.

Polynucleotide sequences are provided, which code for fusion proteins that include first polypeptides and second polypeptides comprising carboxy terminal sequences that increase stability of the first polypeptides against proteolytic degradation, where at least one of the last three amino acid residues at the carboxy termini of the second polypeptides is altered by amino acid substitution, amino acid insertion, or amino acid deletion. The last two amino acid residues of the carboxy terminal sequences of the second polypeptides may be selected from the group consisting of Arg, Asp, Glu, Gly, His, Lys, Phe, Pro, Trp, and Tyr, and the antepenultimate residue of the carboxy terminal sequence of the second polypeptides may be selected from the group consisting of Asp, Gly, Glu, and His. The last three amino acid residues of the carboxy terminal sequence of the second polypeptide may have the sequence Asp-Lys-Asp, Leu-Glu-Ala, Leu-Lys-Ala, or Leu-Ala-Asp. The polynucleotide sequences may encode first polypeptides that are desaturases. Also provided are vectors that include the above polynucleotide sequences. As well, provided are host cells that include the above polynucleotide sequences. The host cells may be mycobacterial cells.

Method for increasing stability of polypeptides against degradation by proteases are provided, which include the step of altering one or more of the last three amino acid residues at the carboxy termini of the polypeptides, where the alteration is selected from the group consisting of amino acid substitution, amino acid insertion, and amino acid deletion, and where the alteration results in the last two amino acid residues of the carboxy termini sequences of the polypeptides being selected from the group consisting of Arg, Asp, Glu, Gly, His, Lys, Phe, Pro, Trp, and Tyr, and the antepenultimate residue of the carboxy terminal sequences of the polypeptide being selected from the group consisting of Asp, Gly, Glu, and His. In the practice of the methods, the alteration may result in the sequence Asp-Lys-Asp, Leu-Glu-Ala, Leu-Lys-Ala, or Leu-Ala-Asp.

Methods for predicting the relative stability of proteins against degradation by proteases are provided, which include the steps of: (a) identifying the last three residues at the carboxy termini of the proteins; and (b) predicting the stability of the proteins based upon the identity of the last three residues at the carboxy termini of the protein, where when the last two amino acid residues of the carboxy terminal sequence of the proteins are selected from the group consisting of Arg, Asp, Glu, Gly, His, Lys, Phe, Pro, Trp, and Tyr, and the antepenultimate residue of the carboxy terminal sequence of the proteins is selected from the group consisting of Asp, Gly, Glu, and His, the proteins have a relatively increased stability against degradation by proteases.

Methods for predicting the relative stability of proteins against degradation by proteases are provided, which include the steps of: (a) identifying the last two residues at the carboxy termini of the proteins; and (b) predicting the stability of the proteins based upon the identity of the last two residues at the carboxy termini of the proteins, where when the last two amino acid residues of the carboxy terminal sequences of the proteins are selected from the group consisting of Arg, Asp, Glu, Gly, His, Lys, Phe, Pro, Trp, and Tyr, the proteins have a relatively increased stability against degradation by proteases.

BRIEF DESCRIPTION OF THE DRAWINGS

FIG. 1 depicts the vector maps of: (A) pTET derived from pUV15TetORs; (B) pGFP obtained by insertion of GFP with no stop codon.

FIG. 5 is a graph showing residue specificity of the mycobacterial C-terminal directed degradation/proteolysis system.

DETAILED DESCRIPTION OF THE PRESENTLY PREFERRED EMBODIMENTS

Figure 2:
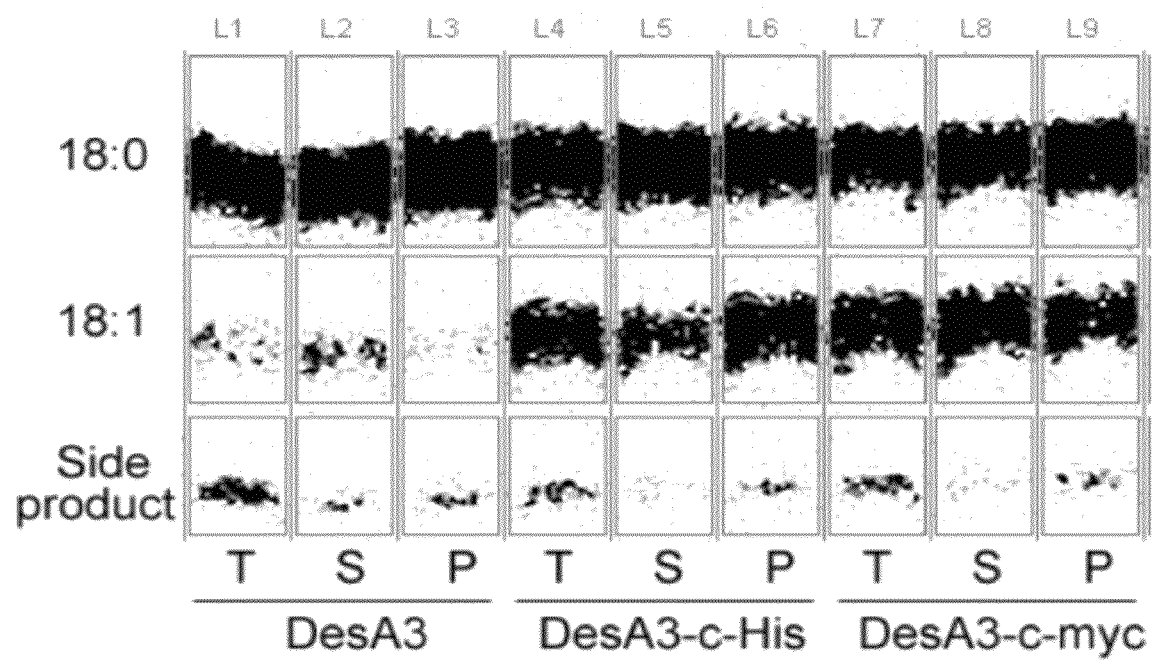
FIG. 2 is an image depicting the effect of adding different C-terminal tags to DesA3 on stearoyl-CoA $\Delta^9$ desaturase activity.

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other organic chemistry techniques are generally performed according to Sambrook et al., 1989, *Molecular Cloning—A Laboratory Manual*, Cold Spring Harbor Laboratory, Cold Spring Harbor, N.Y., N.Y.; Ausubel et al., 1993, *Current Protocols in Molecular Biology*, Volumes 1-3, John Wiley & Sons, Inc., Hoboken, N.J.; Kriegler, 1990, *Gene Transfer and Expression: A Laboratory Manual*, Stockton Press, New York, N.Y.; Overman, 2005, *Organic Reactions*, John Wiley & Sons, Inc., Hoboken, N.J.; and March, 1992, *Advanced Organic Chemistry: Reactions, Mechanisms and*

Structure, 4th Ed., Wiley-Interscience, New York, N.Y., each of which is incorporated herein by reference in its entirety.

"Polynucleotide sequence" or "nucleic acid" refers to a single or double-stranded polymer of deoxyribonucleotide or ribonucleotide bases read from the 5' to the 3' end. Nucleic acids may also include modified nucleotides that permit correct read-through by a polymerase and do not alter expression of a polypeptide encoded by that nucleic acid. "Nucleic acid sequence encoding" refers to a nucleic acid that directs the expression of a specific protein or peptide. The nucleic acid sequences include both the DNA strand sequence that is transcribed into RNA, and the RNA sequence that is translated into protein. The nucleic acid sequences include both the full length nucleic acid sequences as well as non-full length sequences derived from the full length sequences. It should be further understood that the sequence includes the degenerate codons of the native sequence or sequences that may be introduced to provide codon preference in a specific host cell.

A "coding sequence", "coding region", or a sequence that "encodes" a protein or peptide is a nucleic acid sequence which is transcribed into mRNA (in the case of DNA) or translated into a polypeptide (in the case of mRNA) in vitro or in vivo when placed under the control of appropriate regulatory sequences.

"Nucleic acid construct" or "DNA construct" refers to a coding sequence or sequences operably linked to appropriate regulatory sequences so as to enable expression of the coding sequence.

A "polypeptide" is a chain of amino acids linked together by peptide bonds. A "protein" may include one or more polypeptides. The alterations of one or more amino acid residues at the carboxy termini described herein specifically include alterations to both polypeptides and proteins. Thus, reference to a "carboxy terminus of a polypeptide" is meant to also include the carboxy terminus of the protein to which that polypeptide might be a part of. Reference to an "alteration of a carboxy terminus of a polypeptide" is meant to also include an alteration of the carboxy terminus of the protein to which that polypeptide might be a part of.

"C-terminus" (also known as the carboxy terminus, carboxy-terminus, carboxyl terminus, carboxyl-terminus, carboxy-tail, C-tail, C-terminal end, or COOH-terminus) of a protein or polypeptide is the end of the amino acid chain terminated by a free carboxyl group (—COOH). For purposes of the present invention, the C-terminus of a protein or polypeptide encompasses approximately 1-20 amino acids of the C-terminus of a protein or a polypeptide. The convention for writing protein or polypeptide sequences is to put the C-terminal end on the right and write the sequence from N-terminus (left) to C-terminus (right). Reference to a carboxy terminus of a polypeptide is meant to include reference to a carboxy terminus of the protein of which that polypeptide might be part of. The amino acid sequence of a carboxy terminus may include information required for regulating the stability of the polypeptide (or by extension the protein) that the carboxy terminus is a part of. "Last" or "ultimate" C-terminus amino acid residue refers to the last amino acid residue at the C-terminus, at the end of the amino acid chain. "Penultimate" means next to last. "Penultimate residue" of the C-terminus refers to the next to last amino acid residue at the C-terminus. "Antepenultimate" means third from the end. "Antepenultimate" amino acid residue at the C terminus means third from the end residue at the C-terminus. It is contemplated that reference to the end of the carboxy terminus specifically includes reference to the last (ultimate) amino acid residue, next to last (penultimate) amino acid residue, and third from the end (antepenultimate) amino acid residue.

"Stability" of a polypeptide or protein refers to the quality, state, or degree of being stable, and may be manifested, for example, through resistance of the polypeptide or protein to degradation such as chemical or physical disintegration. Proteins can become less stable and can therefore lose activity as a result of many factors, such as proteolysis, aggregation, and suboptimal buffer conditions. It is specifically contemplated that stability of a polypeptide (and by extension of a protein to which that polypeptide may belong) refers to the resistance of the polypeptide to proteolytic degradation. For example, stability of a polypeptide (and by extension a protein) may refer to the increased resistance of mycobacterial desaturase DesA3 to degradation by a *M. smegmatis* C-terminal tail specific protease (msTsp). "Increased stability" of a polypeptide with an altered carboxy terminus refers to increased stability of the polypeptide that includes altered carboxy terminus according to the present invention compared to the stability of the unaltered, native, or wild type polypeptide. Protein stability may be quantitatively described by the standard Gibbs energy change, $\Delta G_D°$, involved in unfolding the unique, three dimensional structure to randomly coiled polypeptide chains (Hinz et al., 1993, *Pure and Appl. Chem.* 65: 947-952). In the case of enzymes, stability may be measured as relative loss of a measurable catalytic activity over a period of time.

"Desaturases" refer to enzymes that remove two hydrogen atoms from adjacent carbons in an organic compound, creating a carbon/carbon double bond. Such enzymes can be found in humans and other eukaryotes (such as monkeys, rats, mice, zebra fish, cows, pigs, sheep, chickens, yeast, and others), in beneficial microorganisms (such as *Streptomyces colieocolor*, *Streptomyces avermitilis* and other bacteria that are responsible for the synthesis of a wide array of antibiotics), and in pathogens (such as *Mycobacterium tuberculosis, Mycobacterium leprae, Mycobacterium bovis, Mycobacterium avis*, and many other Gram-positive actinomycetes).

"Isolated" or "purified" refer to material that is substantially or essentially free from components that normally accompany it as found in its native state. Purity and homogeneity are typically determined using analytical chemistry techniques such as polyacrylamide gel electrophoresis or high performance liquid chromatography. The term "isolated protein" or "isolated polypeptide," as used herein, means that a subject protein (1) is free of at least some other proteins with which it would typically be found in nature, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or noncovalent interaction) with portions of a protein with which the "isolated protein" is associated in nature, (6) is operably associated (by covalent or noncovalent interaction) with a polypeptide with which it is not associated in nature, or (7) does not occur in nature. Such an isolated protein can be encoded by genomic DNA, cDNA, mRNA or other RNA, of synthetic origin, or any combination thereof. Preferably, the isolated protein is substantially free from proteins or polypeptides or other contaminants that are found in its natural environment that would interfere with its use (therapeutic, diagnostic, prophylactic, research or otherwise). Alternatively, the isolated protein is sufficiently free from proteins or polypeptides or other contaminants that are found in its natural environment that the isolated protein is capable of being used (for therapeutic, diagnostic, prophylactic, research or other applications) in a manner that it could not be used in its natural environment.

In general, a polypeptide "homolog" includes any homolog in which residues at a particular position in the sequence have been substituted by other amino acids, and further includes the possibility of inserting an additional residue or residues between two residues of the parent protein as well as the possibility of deleting one or more residues from the parent sequence. Any amino acid substitution, insertion, or deletion is encompassed by the invention. In some embodiments, the amino acid substitution is a conservative substitution. Conservative substitutions whereby an amino acid of one class is replaced with another amino acid of the same type fall within the scope of the invention so long as the substitution does not materially alter the biological activity of the compound. For example, a homolog of SEQ ID NO:83 shares the same amino acid sequence as SEQ ID NO:83 except for a few amino acid differences, e.g. substitutions, insertions, or deletions.

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the sequence is complementary to all or a portion of a reference polynucleotide sequence.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 25% sequence identity. Alternatively, percent identity can be any integer from 25% to 100%. More preferred embodiments include at least: 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98% or 99% identity compared to a reference sequence using the programs described herein; preferably BLAST using standard parameters, as described. One of skill will recognize that these values can be appropriately adjusted to determine corresponding identity of proteins encoded by two nucleotide sequences by taking into account codon degeneracy, amino acid similarity, reading frame positioning and the like.

Substantial identity of amino acid sequences for these purposes normally means sequence identity of at least 40%. Preferred percent identity of polypeptides can be any integer from 40% to 100%. More preferred embodiments include at least 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% identity compared to a reference sequence using the programs described herein; preferably BLAST using standard parameters, as described. Polypeptides that are "substantially similar" share sequences as noted above except that residue positions which are not identical may differ by conservative amino acid changes.

Conservative amino acid substitutions refer to the interchangeability of residues having similar side chains and preferably have similar physical/chemical properties. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, aspartic acid-glutamic acid, and asparagine-glutamine. Accordingly, polynucleotides of the present invention encoding a polypeptide of the present invention include nucleic acid sequences that encode polypeptides with one or more conservative amino acid substitutions.

The number of conservative amino acid substitutions is any integer, for example any integer from 1 to 1000. Thus, with respect to a polypeptide sequence that has 300 amino acids, the number of conservative amino acid substitutions may be about 10%, i.e., 1 to 30 conservative amino acid substitutions, for example 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 substitutions. In some embodiments, polypeptides or proteins of the present invention include amino acid sequences that have substantial identity to the amino acid sequences of the present invention.

A "non-naturally-occurring polypeptide" or a "non-native polypeptide" is any polypeptide having an amino acid sequence that is not found in nature. Thus, a non-naturally-occurring polypeptide can be an altered version of a naturally-occurring polypeptide, or an engineered polypeptide. For example, a non-naturally-occurring polypeptide having desaturase activity can be an altered version of a naturally-occurring polypeptide having desaturase activity that retains at least some desaturase activity. A polypeptide can be altered by, for example, one or more amino acid additions, deletions, and/or substitutions. The present invention specifically contemplates alterations of one or more of the ultimate, penultimate, and/or antepenultimate amino acid residues of the polypeptides. It is important to note that a polypeptide having a particular enzymatic activity can be a polypeptide that is either naturally-occurring or non-naturally-occurring.

"Combinatorial substitution" refers to the substitution of one or more amino acids in a peptide, polypeptide, and/or protein molecule. Combinatorial chemistry may be used for combinatorial substitution(s) of desired amino acid(s). Combinatorial chemistry may include wet chemistry, the rapid synthesis of various molecules, or the computer simulation of a large number of different but structurally related molecules. Synthesis of molecules in a combinatorial fashion can quickly lead to large numbers of molecules. A molecule (for example a carboxy tail with three amino acid residues) with three points of diversity (R1, R2, and R3) can generate $N_{R1} \times N_{R2} \times N_{R3}$ possible structures, where $N_{R1}$, $N_{R2}$, and $N_{R3}$ are the number of different substituents utilized. Combinatorial substitution may be used to alter any number of desired amino acid residues according to the present invention.

For example, the change in 18:1-CoA production can be used for determination of the activity of an expressed enzyme such as desaturase, which can be an indicator of the stability of the desaturase. An example of a method for assay of 18:1-CoA production is provided as follows. Radioactive fatty acyl-CoAs are obtained from American Radiolabeled Chemicals (St. Louis, Mo.). The reaction mixture contains 20 mM of potassium phosphate and 150~250 mM of NaCl in a total reaction volume of 200 μL. Aliquots (20 μL) of the *M. smegmatis* pVV16 or pVV16-DesA3 total lysate, supernatant or pellet fractions are added in various combinations with aliquots (15 μL) of supernatant fraction prepared from either *E. coli* pQE80 or pQE80-Rv3230c. The reaction is initiated by addition of 0.4 μmol of NADPH, 6 nmol of stearoyl-CoA, 0.03 μCi of [1-$^{14}$C]-stearoyl-CoA and 0.2 nmol of FAD in a combined volume of 200 μL. The reaction is incubated at 37° C. for 1 h and stopped by the addition of 200 μL of 2.5 M KOH in ethanol. The mixture is heated at 80° C. for 1 h and acidified by the addition of 280 μL of formic acid. The saponified fatty acids are extracted with 700 μL of hexane, 200 μL of the extract is evaporated to dryness, resuspended in 50 μL of hexane and separated into saturated and unsaturated acids on a 10% AgNO$_3$-impregnated thin-layer chromatography plate using chloroform:methanol:acetic acid:water (90:8:1:0.8) as the developing solvent. Radioactivity is counted by phosphorimaging using a Packard Instant Imager (Packard, Meriden, Conn.) for 30-60 min. Samples prepared in this manner give ~200 total imager units for the major radioactive bands detected, which is within the linear response range of the instrument. Reactions performed with stearoyl-CoA were also treated by thin-layer chromatography as described above, and the individual bands are extracted from the plate, methylated and analyzed by GC/MS to determine fatty acid content.

The compositions and methods of the present invention provide for the identification of amino acid residues and sequences that increase protein stability. The increase of protein stability may refer to the increased stability of the polypeptides or proteins against processing. For example, U.S. Pat. No. 5,290,690, incorporated herein by reference, discloses methods and means for controlling the stability of proteins. The identification of residues critical for regulation of protein stability has been described by Pereira et al., 2003, *J. Biol. Chem.* 278: 6816-6823, which is incorporated herein by reference. The methods of the invention are particularly useful for increasing the stability and/or utilization of polypeptides that have enzymatic activities. Alternatively, the compositions and methods of the present invention provide for the identification of amino acid residues and sequences that promote protein degradation processes, such as proteolytic processes.

In one aspect, the invention involves genetically engineering a system for the expression of enzymes involved in fatty acid desaturation. The genetic engineering may include increasing the stability of enzymes involved in desaturation. For example, the proteolytic degradation of one or more enzymes involved in fatty acid desaturation may be reduced or stopped. However, in other instances, the genetic engineering may additionally include expression of other non-enzymatic components that are involved in desaturation. The compositions and methods of the present invention are thus useful for the expression of systems for desaturation of fatty acids, in which the polypeptides may be more stable if they, and in particular their carboxy termini, are genetically engineered according to the present invention.

One method of expression of the proteins of this invention is through the use of vectors such as plasmids, phage, phagemids, viruses, artificial chromosomes and the like. Preferred vectors are expression vectors. Expression vectors contain a promoter that may be operably linked to a coding region. A gene or coding region is operably linked to a promoter when transcription of the gene initiates from the promoter. More than one gene may be operably linked to a single promoter. In one aspect, the vector is introduced into an organism that is suitable for gene and protein expression.

A variety of expression vectors may be used for expression in *E. coli*, insect, yeast, or mammalian cells. Expression vectors that may be used include, but are not limited to, the Gateway® Destination vectors (Invitrogen, Carlsbad, Calif.), pQE-30, pQE-40, and pQE-80 series (Qiagen, Valencia, Calif.), pUC19 (Yanisch-Perron et al., 1985, *Gene* 33: 103-119), pBluescript II SK+ (Stratagene, La Jolla, Calif.), the pET system (Novagen, Madison, Wis.), pLDR20 (ATCC 87205), pBTrp2, pBTac1, pBTac2 (Boehringer Ingelheim Co., Ingelheim, Germany), pLSA1 (Miyaji et al., 1989, *Agric. Biol. Chem.* 53: 277-279), pGEL1 (Sekine et al., 1985, *Proc. Natl. Acad. Sci. USA.* 82: 4306-4310), and pSTV28 (manufactured by Takara Shuzo Co., Shimogyo-ku, Kyoto 600-8688, Japan). When a yeast strain is used as the host, examples of expression vectors that may be used include pYEST-DES52 (Invitrogen, Carlsbad, Calif.), YEp13 (ATCC 37115), YEp24 (ATCC 37051), and YCp50 (ATCC 37419). When insect cells are used as the expression host, examples of expression vectors that may be used include pVL1393 (BD Biosciences, Franklin Lakes, N.J.) and pIEX (Novagen, Madison, Wis.).

Alternatively, expression kits might be utilized for cell-free protein expression. For example, the EasyXpress Protein Synthesis Mini Kit, the EasyXpress Protein Synthesis Mega Kit (Qiagen), the In vitro Director™ System (Sigma-Aldrich, St. Louis, Mo.), the TnT Sp6 High-Yield Protein Expression System (Promega; Madison, Wis.) or the WePro lysate (Cell Free Sciences, Yokohama, Japan) might be used. Examples of expression vectors used for cell-free protein expression include pIX4 (Qiagen; Valencia, Calif.) and pEU (Cell Free Sciences, Yokohama, Japan).

Protein expression can be controlled with the use of desirable promoters. Essentially any promoter may be used as long as it can be expressed in the engineered organism. Examples of preferred promoters for expression of proteins in *Mycobacterium smegmatis* are the tetracycline resistance gene promoter (Ehrt et al., 2005, *Nucleic Acids Res.* 33: e21) and the acetamidase gene promoter (Parish et al., 1997, *Microbiology* 143: 2267-2276). Examples of preferred promoters for expression of proteins in *E. coli* are the lambda P$_R$ promoter and the lac promoter. When the organism is a yeast cell, any promoter expressed in the yeast strain host can be used. Examples include the gal 1 promoter, gal 10 promoter, heat shock protein promoter, MF alpha 1 promoter, and CUP 1 promoter.

A ribosome-binding sequence (RBS) in prokaryotes, or an internal ribosome entry site (IRES) in eukaryotes, may be operably linked to the polynucleotide that is expressed. The RBS or IRES is operably linked to the polynucleotide that is expressed when it directs proper translation of the protein encoded by the polynucleotide. It is preferred that the RBS or IRES is positioned for optimal translation of the linked coding region (for example, 6 to 18 bases from the initiation codon). In vectors containing more than one polynucleotide, it is preferred that each coding region is operably linked to an RBS or IRES.

The carboxy terminus of the polypeptide may be altered prior to insertion of the coding sequence into or within the expression vector. These alterations may include one or more changes, deletions, additions, and/or substitutions of the amino acid residues in the carboxy terminus. When alterations are made, the alterations may result in maintaining a desired enzymatic function and/or specificity of the enzyme. In other embodiments, alterations may be made so that the enzymatic function of the enzyme is increased and/or specificity of the enzyme is increased. In yet another embodiment, alterations may be made so that the enzymatic function of the enzyme is decreased and/or specificity of the enzyme is decreased.

When a heterologous gene is to be introduced into an organism that does not naturally encode the gene, optimal expression of the gene may require alteration of the codons to better match the codon usage of the host organism. The codon usage of different organisms is well known in the art.

The coding region also may be altered to ease the purification or immobilization of the expressed protein. An example of such an alteration is the addition of a "tag" to the protein. Examples of tags include FLAG, polyhistidine, biotin, T7, S-protein, myc-, and GST (Novagen; pET system). In a preferred embodiment, the gene is altered to contain a hexo-histidine tag in the N-terminus. The protein may be purified by passing the protein-containing solution through a $Ni^{2+}$ column.

In one embodiment, the invention provides compositions and methods to predict and improve the stability of proteins expressed in prokaryotes, and in particular in mycobacteria, for example in M. smegmatis. In particular, the identity of the last two or three residues of the C terminus is a predictor and determinant of the protein stability. At the last (ultimate) residue of the C terminus and the next to last (penultimate) position, substitution to residues with charged side chains, large non-polar side chains, or no side chains can be used to increase the stability of the protein, i.e. to reduce or inhibit the protein degradation. Moreover, at the antepenultimate, third from end position at the C terminus, residues with acidic side chains or with no side chains can be used to increase the stability of the protein, i.e. to reduce or inhibit the protein degradation. The type of protein degradation may include proteolysis.

Amino acid residues with charged side chains include Arg (R), Asp (D), Glu (E), His (H), and Lys (K). Amino acid residues with hydrophobic side chains include Ala (A), Cys (C), Ile (I), Leu (L), Met (M), Pro (P), and Val (V). Amino acids with aromatic side chains include Phe (F), Trp (W), and Tyr (Y). Amino acids with polar side chains include Asp (D), Asn (N), Gln (O), Glu (E), Ser (S), and Thr (T). Amino acids with acidic side chains refer to hydrophilic amino acids having a side chain pK value of less than 7; suitable examples include Glu (E) and Asp (D). Amino acid residues with no side chains include Gly (G). As will be appreciated by those of skill in the art, the above-defined categories are not mutually exclusive. Thus, amino acids having side chains exhibiting two or more physical-chemical properties can be included in multiple categories.

In various aspects of the invention, differently altered forms of proteins are expressed. For example, the alterations of the C termini of these proteins may include one or more amino acid substitutions, one or more amino acid additions, one or more amino acid deletions, truncations, or other alterations known in the art. In some examples, the alterations may be performed using standard amino acids. In other examples, the alterations may be performed using amino acid residues that include modifications such as carboxylation, acetylation, hydroxylation, and the like.

In some embodiments, different variants of the genes or proteins may be expressed. These include homologs, mutants, proteins with amino acids substitutions, etc.

The coding regions of two or more polypeptides may be linked to create a fusion protein with a desired carboxy terminus. In some embodiments, a desaturase-GFP fusion protein with a desired carboxy terminus is expressed. In other embodiments, a desaturase-cytochrome b5 fusion protein with a desired carboxy terminus is expressed. In yet other embodiments, a desaturase-cytochrome b5 reductase fusion protein with a desired carboxy terminus is expressed.

In one embodiment, the invention provides for the recombinant expression of altered proteins of a desaturation complex that are involved in fatty acid desaturation. These altered proteins may be enzymes such as desaturase and oxidoreductase. For example, the desaturase may exist as a separate enzyme or may be a genetic fusion with an oxidoreductase, an oxidoreductase domain, with a reporter protein such as Green Fluorescent Protein, or with any other desired protein. Using the methods of the present invention, C-tail alterations of these proteins or protein constructs may be performed to regulate and to achieve desired stability of the expressed proteins, to increase or to decrease the stability of the expressed proteins against degradation.

In a different embodiment, the invention provides a cell-free expression system for expression of one or more desired proteins with desired carboxy termini, for example desaturases, where genes that encode the proteins are added to the system, proteins are expressed, and enzymatic activities are determined.

In some aspects, the present invention contemplates the analysis of the stability of proteins that may be native. As well, the proteins that are analyzed and/or altered according to the present invention may be recombinant; they may be heterologous proteins that are expressed in prokaryotic hosts. For example, combinatorial substitution of only the last three residues of desaturase DesA3 from Mycobacterium tuberculosis can make the enzyme more stable during heterologous expression in Mycobacterium smegmatis. Thus, as shown in the examples section below, DesA3 variants with the last three amino acids substituted from LAA to either DKD or LEA gave up to 13-fold higher stearoyl-CoA Δ9 desaturase activity as compared to native DesA3 alone. Conversely, alteration of the final three residues of the carboxy terminus of a protein into LAA should increase the degradation of the protein. In particular, when expressed in mycobacteria, such protein should be increasingly degraded by a mycobacterial protease that targets the residues at the C-terminus, in comparison to the wild type, native protein. Moreover, the DKD or LEA variants shown below support the conclusion that alteration of only two residues in the native protein sequence (last and penultimate amino acid residues) is sufficient to impart the increased protein stability against degradation. In some embodiments of the invention, to increase the stability of the expressed proteins, preferred triplets at the end of the C-termini include, but are not limited to, DKD, LEA, LKA, and LAD.

In one embodiment of the present invention, the role of any given or suitably altered C-terminal sequence in the stability of the desired protein against degradation may be examined by use of enhanced folding GFP fused to the desired polypeptide that includes the altered C-terminal sequence.

In one embodiment, the present invention relates to alterations of DesA3 that are resistant to degradation by a M. smegmatis C-terminal tail specific protease (msTsp) when expressed in that organism. In one embodiment of the present invention, it is provided that the last three C-terminal positions of the native DesA3 enzyme C-terminal are the strongest determinants to the proteolytic degradation of DesA3 expressed in M. smegmatis by a M. smegmatis C-terminal tail specific protease (msTsp). Tsp recognizes a relatively apolar C-terminal sequence, for example WVAAA (SEQ ID NO: 80) or LAA, while proteins having a polar C-terminal sequence, for example RSEYE (SEQ ID NO:81) are stable and are not cleaved, i.e. are not degraded. The identities of the last three C-terminal residues of the protein sequence are the most important determinants of the rate of reaction, and small, uncharged residues (Ala, Cys, Ser, Thr, Val) are preferred for proteolytic processing. To decrease the stability of the protein and to increase degradation by proteolysis, non-polar residues are preferred at the penultimate and antepenultimate positions, but larger and more hydrophobic side chains are also acceptable at these positions. To increase the stability of the protein and to decrease degradation by proteolysis, charged or polar residues are preferred at the ultimate and penultimate positions, and the residues Asp, Gly, Glu or His are preferred at the antepenultimate position.

In some embodiments, at the C terminus and the penultimate position, substitution to amino acid residues with charged side chains, residues with large non-polar side chains, and/or no side chain, could be used to inhibit protein degradation. For example, alterations of one or more amino acids at the C terminus of a polypeptide could reduce or inhibit the proteolysis of the polypeptide. Moreover, at the third position from the C terminus, residues with no side chain or residues with acidic side chains may be preferred to inhibit degradation such as proteolysis. Therefore, combinational substitution of only the last three residues of a protein such as DesA3 can make the enzyme more stable during heterologous expression in *M. smegmatis*. As shown in the examples section below, DesA3 variants with the last three amino acids substituted from LAA to either DKD or LEA gave up to 13-fold higher stearoyl-CoA Δ9 desaturase activity as compared to DesA3 alone. Moreover, the DKD or LEA variants were comparable in activity to DesA3-c-myc, supporting the conclusion that alteration of only two residues in the native protein sequence is sufficient to impart the increased stability. Consequently, the compositions and methods of the present invention may be used in an approach to predict and improve the stability of other proteins expressed in *M. smegmatis*, in other mycobacterial hosts, and in other prokaryotic hosts.

The compositions and methods of the present invention may be used to predict and regulate, for example improve, the stability of recombinant proteins expressed in *M. smegmatis*. In one example, it is contemplated that the present invention is useful for high throughput screening assays for DesA3, i.e. stearoyl-CoA Δ9 desaturase, activity. As well, the compositions and methods of the present invention may be used to modify heterologous protein sequences to better overproduce important bioactive targets. For example, the compositions and methods of the present invention may be used to increase the stability of expressed DesA3, an essential enzyme in *Mycobacterium tuberculosis*, and one that cannot be successfully expressed in *Escherichia coli*. Not wanting to be bound by the following theory, since most proteases are conserved in bacterial genera, the results herein indicate that similar C-terminal specific protease systems may be used by *M. tuberculosis* and other pathogenic mycobacteria to regulate protein turnover.

It is to be understood that this invention is not limited to the particular methodology, protocols, or reagents described, and as such may vary. It is also to be understood that the terminology used herein is for the purpose of describing particular embodiments only, and is not intended to limit the scope of the present invention, which is limited only by the claims. The following examples are offered to illustrate, but not to limit the claimed invention. All publications, patents, and patent applications cited herein are hereby incorporated by reference in their entirety for all purposes.

EXAMPLES

DNA and Plasmid Reagents

Table 1 lists examples of the bacterial strains and plasmids used in this work. The tetracycline-inducible mycobacterial expression vector pUV15TetORs (Ehrt et al., 2005, *Nucleic Acids Res.* 33:e21) was obtained from Prof. Sabine Ehrt (Department of Microbiology and Immunology, Weill Medical College, Cornell University, Ithaca, N.Y.), and was modified herein. In brief, the vector pUV15TetORs was digested using PacI and EcoRV and the digested vector was ligated to the annealed multiple cloning site linker primers. The primers were: L1: AACAGCTGGCGATCGCCAGTACTGGATCCCCTGCA GGCTTAAGATTTAAATGAT (SEQ ID NO:75); L2: ATCATTTAAATCTTAA GCCTGCAGGGGATCCAGTACTGGCGATCGCCAGCTGTTAAT (SEQ ID NO:76), and they contained compatible cohesive ends to create pTET.

The vector pGFP was created to study expression of GFP with an altered C-terminus. The GFP variant with enhanced folding efficiency and fluorescence yield (Scholz et al., 2000, *Eur. J. Biochem.* 267: 1565-1570) was amplified from pUV15TetORs and cloned into pTET using the PacI and Asi SI sites introduced in the multicloning site. A control vector pGFPStop that contained a stop codon after GFP was made in the same way. The maps of pTET and pGFP are shown in FIG. 1. Shown in FIG. 1(A) is a vector map of pTET, which is derived from pUV15TetORs (Ehrt et al., 2005, *Nucleic Acids Res.* 33:e21). This vector contains a tetracycline-inducible promoter (tetO), a multiple cloning site (MCS), transcription terminators (T), constitutively expressed tetracycline repressor cassette (puv15-tetR), hygromycin resistance cassette (hygR), a mycobacterial replication origin (MYC ori) and an *E. coli* replication origin (COLE1 ori). Shown in FIG. 1(B) is a vector map of pGFP obtained by insertion of GFP with no stop codon.

Total genomic DNA of *Mycobacterium tuberculosis* H37Rv was obtained from the TB Research Materials Facility at Colorado State University, Fort Collins, Colo. (Prof. J. Belisle, Director, NIH NIAD NO1AI75320). This material was used to clone rv3229c and rv3230c by PCR. Pfu DNA polymerase was from Stratagene (La Jolla, Calif.). Oligonucleotide primers were obtained from Integrated DNA Technologies, Inc. (Coralville, Iowa). The pSMART-HC Amp CloneSmart blunt cloning kit (Lucigen, Middleton, Wis.) was used for initial cloning and sequencing in *E. coli*.

The expression vector pQE80 (Qiagen, Valencia, Calif.) was used to express Rv3230c in *E. coli* (Table 1). The shuttle/expression vector pVV16 (Jackson et al., 2000, *J. Biol. Chem.* 275: 30092-30099) was used to express DesA3 either with or without a C-terminal His6-tag under the control of the transcriptional and translational signals of the hsp60 promoter in *M. smegmatis* (ATCC 700084). The vector pMYC (modified from pVV16) was used to express DesA3 with a C-terminal myc tag or with two variations of the C-terminal amino acid sequence. Big Dye DNA sequencing (Applied Biosystems, Foster City, Calif.) was performed in the University of Wisconsin Biotechnology Center to verify the coding sequence of the expression plasmids. Table 1 summarizes the used strains and DNA constructs.

TABLE 1

Bacterial strains and plasmids used in this work

| Strain or plasmid | Relevant characteristics | Source or Reference |
|---|---|---|
| Strains | | |
| *Escherichia coli* strain *E. cloni* 10G | F-mcrA Δ(mrr-hsdRMS-mcrBC) endA1 recA1 φ80dlacZΔM15 ΔlacX74 araD139 Δ(ara, leu) 7697 galU galK rpsL nupG λ-tonA | Lucigen |
| *E. coli* Rosetta2 | F– ompT hsdS$_B$(r$_B^-$ m$_B^-$) gal dcm pRARE2 (cam$^R$ and tRNA genes argU, argW, argX, ileX, glyT, leuW, proL, metT, thrT, tyrU, and thrU) | Novagen |
| *Mycobacterium smegmatis* mc²155 | Mycobacterial expression host with high transformation efficiency | ATCC 700084 |
| Plasmids | | |
| pQE80 | Commercially available *Escherichia coli* expression vector | Qiagen |
| pVV16 | Shuttle vector and mycobacterial expression vector controlled by constitutive Hsp60 promoter | Jackson et al., 2000 |
| pMYC | Derived from PVV16 to express target genes with a C-terminal myc tag | This work |
| pQE80-Rv3230c | rv3230c in pQE80 | Chang and Fox, 2006 |
| pVV16-DesA3 | desA3 in pVV16 | Chang and Fox, 2006 |
| pVV16-DesA3-His6 | desA3-His6 in pVV16 | This work |
| pMYC-DesA3-myc | DesA3-myc expressed from pMYC | This work |
| pMYC-DesA3-DKD | DesA3 with the last three amino acid changed from LAA to DKD expressed from pMYC | This work |
| pMYC-DesA3-LEA | DesA3 with the last three amino acid changed from LAA to LEA expressed from pMYC | This work |
| pUV15TetORs | Cloning shuttle vector and mycobacterial expression vector controlled by tetracycline inducible promoter | Ehrt et al., 2005 |
| pTet | Modified from pUV15TetORs to replace the original GFP gene with a useful multi-cloning site for further cloning work | This work |
| pGFPStop | Enhanced GFP gene with a stop codon in the multi-cloning site of pTet | This work |
| pGFP | Enhanced GFP gene without a stop codon in the multi-cloning site of pTet. This vector was used to make the constructs with variations in DesA3 C-terminal described below. | This work |
| pGFP-DesA3-LAA | Expression of the GFP with a C-terminal fusion to native DesA3-LAA | This work |
| pGFP-DesA3-LAK | Expression of the GFP with a C-terminal fusion to native DesA3-LAK | This work |
| pGFP-DesA3-LAD | Expression of the GFP with a C-terminal fusion to native DesA3-LAD | This work |
| pGFP-DesA3-LKA | Expression of the GFP with a C-terminal fusion to native DesA3-LKA | This work |
| pGFP-DesA3-LDA | Expression of the GFP with a C-terminal fusion to native DesA3-LDA | This work |
| pGFP-DesA3-KAA | Expression of the GFP with a C-terminal fusion to native DesA3-KAA | This work |
| pGFP-DesA3-DAA | Expression of the GFP with a C-terminal fusion to native DesA3-DAA | This work |

Cloning of DesA3

The untagged rv3229c gene (encoding DesA3) and the rv3229c gene modified to encode C-terminal His6- or myc-tagged DesA3 were all amplified using *M. tuberculosis* total genomic DNA and primers shown in Table 2. The PCR contained 10% dimethyl sulfoxide and consisted of 30 cycles of melt, anneal, and extend at temperatures of 94° C., 55° C., and 72° C., respectively. The resulting DNA fragments were purified by gel electrophoresis and extracted using a QIAquik gel extraction kit (Qiagen). The PCR product was ligated into pSMART-HCAmp for sequencing. A plasmid with correct sequence was digested with NdeI and HindIII, and ligated into the similarly digested pVV16 or pMYC to create expression vectors pVV16-DesA3, pVV16-DesA3-His6, or pMYC-DesA3-myc. *E. cloni* 10G transformants containing these plasmids were cultured on either Luria-Bertani broth or agar medium containing 50 μg/mL of kanamycin. Table 2 summarizes the primers used for gene amplification.

TABLE 2

Primers used for amplification of different variations of the desA3 gene

| Protein construct[a] | 5' primer[b] | 3' primer[c] |
|---|---|---|
| Native DesA3 | 5'-gggaattcCATATGgcgatcactg-acgtcgacgtattcgcg-3' (SEQ ID NO: 1) | 5'-cccAAGCTTttaggctgccagatcgtc-gggttcgg-3' (SEQ ID NO: 2) |
| DesA3-His6 | 5'-gggaattcCATATGgcgatcactg-acgtcgacgtattcgcg-3' (SEQ ID NO: 3) | 5'-cccAAGCTTggctgccagatcgtcggg-ttcgg-3' (SEQ ID NO: 4) |
| DesA3-c-myc | 5'-gggaattcCATATGgcgatcactg-acgtcgacgtattcgcg-3' (SEQ ID NO: 5) | 5'-cccAAGCTTggctgccagatcgtcggg-ttcgg-3' (SEQ ID NO: 6) |
| DesA3-DKD | 5'-gggaattcCATATGgcgatcactg-acgtcgacgtattcgcg-3' (SEQ ID NO: 7) | 5'-cAAGCTT ttagtccttgtcatcgtcgggttcggtgaccg-3' (SEQ ID NO: 8) |
| DesA3-LEA | 5'-gggaattcCATATGgcgatcactg-acgtcgacgtattcgcg-3' (SEQ ID NO: 9) | 5'-cAAGCTT ttaggcctccagatcgtcgggttcggtgaccg-3' (SEQ ID NO: 10) |
| GFP-DesA3 | 5'-cccGCGATCGCCatggcgatc-actgacgtcgac-3' (SEQ ID NO: 11) | 5'-taATTTAAATctattaggctgccagatcgtc gggttc-3' (SEQ ID NO: 12) |

TABLE 2-continued

Primers used for amplification of different variations of the desA3 gene

| Protein construct[a] | 5' primer[b] | 3' primer[c] |
|---|---|---|
| GFP-DesA3-LAK | | 5'-taATTTAAATctattactttgccagatcgtcg ggttcgg-3' (SEQ ID NO: 13) |
| GFP-DesA3-LAD | | 5'-taATTTAAATctattagtctgccagatcgtcg ggttcgg-3' (SEQ ID NO: 14) |
| GFP-DesA3-LKA | | 5'-taATTTAAATctattaggccttcagatcgtcg ggttcggtgaccg-3' (SEQ ID NO: 15) |
| GFP-DesA3-LDA | | 5'-aATTTAAATctattaggcgtccagatcgtcg ggttcggtgaccg-3' (SEQ ID NO: 16) |
| GFP-DesA3-KAA | | 5'-taATTTAAATctattaggctgccttatcgtcg ggttcggtgaccgac-3' (SEQ ID NO: 17) |
| GFP-DesA3-DAA | | 5'-taATTTAAATctattaggctgcgtcatcgtcg ggttcggtgaccgac-3' (SEQ ID NO: 18) |

[a]Protein constructs are *M. tuberculosis* DesA3 with the indicated C-terminal fusions or GFP with full-length DesA3 (DesA3) or GFP with a C-terminus of DesA3 having the last residues indicated.
[b]The NdeI and Asi SI restriction sites are shown in capital letters.
[c]The HindIII and SwaI restriction sites are shown in capital letters.

The desA3 gene was amplified to mutate the C-terminal LAA residues to either DKD or LEA using the primers shown in Table 2. The PCR and cloning steps were the same as those used for the cloning of DesA3 into pMYC described above. These two expression vectors were named pMYC-DesA3-DKD and pMYC-DesA3-LEA, respectively.

Cloning of GFP Fused to DesA3

The desA3 gene or variants with alterations at the 3' end were amplified using the forward and reverse primers shown in Table 2. The PCR steps were the same as those used for the cloning of DesA3 described above. After a pSMART-HCAmp plasmid with the correct sequence was identified, it was digested with Asi SI and SwaI and the insert was ligated into the similarly digested pGFP. The individual *E. coli* transformants containing these plasmids were cultured on either Luria-Bertani broth or agar medium containing 200 μg/mL of hygromycin. These vectors were used to express GFP with a C-terminal fusion to either native DesA3 or to variants containing single Lys or Asp substitutions in each of the last three amino acids of the native enzyme, LAA.

Cloning of GFP Fused to DesA3 C-Terminal Peptides

Primer pairs encoding several variations of the codons for the last 12 residues from DesA3 or from Msmeg_1886, the homologous desaturase from *M. smegmatis*, are listed in Table 3. Vector pGFP was digested using Asi SI and SwaI and the annealed primer pairs, containing the compatible cohesive ends, were ligated to the digested vector. The individual *E. coli* transformants containing these plasmids were cultured on either Luria-Bertani broth or agar medium containing 200 μg/mL of hygromycin. The presence of the DNA sequence encoding the desired variation was confirmed by sequencing in the reverse direction. These vectors were used to express GFP with a C-terminal fusion to the different variations of the last 12 amino acids from DesA3 or to the native C-terminal of Msmeg_1886. Table 3 summarizes the primers used for direct ligation.

TABLE 3

Primer pairs used to modify five residues at the C-terminus of modified GFP shown in FIG. 5

| Construct[a] | Primer pair |
|---|---|
| DDLAA | G1F: CGCCGCTAAGTCGGTCACCGAACCCGACGATCTGGCAGCCTAATAG (SEQ ID NO: 19) G1R: CTATTAGGCTGCCAGATCGTCGGGTTCGGTGACCGACTTAGCGGCGAT (SEQ ID NO: 20) |
| AKRAA | G11F: CGCCGGCTGGCGCCGGTCGAGCCGGGCCAAGCGCGCCGCCTAGTAA (SEQ ID NO: 21) G11R: TTACTAGGCGGCGCGCTTGGCCCGGCTCGACCGGCGCCAGCCGGCGAT (SEQ ID NO: 22) |

TABLE 3-continued

Primer pairs used to modify five residues at the C-terminus of modified GFP shown in FIG. 5

| | Primer pair |
|---|---|
| AKRAD | G12F:<br>CGCCGGCTGGCGCCGGTCGAGCCGGGCCAAGCGCGCCGACTAGTAA<br>(SEQ ID NO: 23)<br>G12R:<br>TTACTAGTCGGCGCGCTTGGCCCGGCTCGACCGGCGCCAGCCGGCGAT<br>(SEQ ID NO: 24) |

Position 1

| | |
|---|---|
| DDLAK | G2F:<br>CGCCGCTAAGTCGGTCACCGAACCCGACGATCTGGCAAAGTAATAG<br>(SEQ ID NO: 25)<br>G2R:<br>CTATTACTTTGCCAGATCGTCGGGTTCGGTGACCGACTTAGCGGCGAT<br>(SEQ ID NO: 26) |
| DDLAR | G17F:<br>CGCCGCTAAGTCGGTCACCGAACCCGACGATCTGGCACGCTAATAG<br>(SEQ ID NO: 27)<br>G17R:<br>CTATTAGCGTGCCAGATCGTCGGGTTCGGTGACCGACTTAGCGGCGAT<br>(SEQ ID NO: 28) |
| DDLAD | G3F:<br>CGCCGCTAAGTCGGTCACCGAACCCGACGATCTGGCAGACTAATAG<br>(SEQ ID NO: 29)<br>G3R:<br>CTATTAGTCTGCCAGATCGTCGGGTTCGGTGACCGACTTAGCGGCGAT<br>(SEQ ID NO: 30) |
| DDLAE | G16F:<br>CGCCGCTAAGTCGGTCACCGAACCCGACGATCTGGCAGAGTAATAG<br>(SEQ ID NO: 31)<br>G16R:<br>CTATTACTCTGCCAGATCGTCGGGTTCGGTGACCGACTTAGCGGCGAT<br>(SEQ ID NO: 32) |
| DDLAH | G18F:<br>CGCCGCTAAGTCGGTCACCGAACCCGACGATCTGGCACACTAATAG<br>(SEQ ID NO: 33)<br>G18R:<br>CTATTAGTGTGCCAGATCGTCGGGTTCGGTGACCGACTTAGCGGCGAT<br>(SEQ ID NO: 34) |
| DDLAG | G27F:<br>CGCCGCTAAGTCGGTCACCGAACCCGACGATCTGGCAGGCTAATAG<br>(SEQ ID NO: 35)<br>G27R:<br>CTATTAGCCTGCCAGATCGTCGGGTTCGGTGACCGACTTAGCGGCGAT<br>(SEQ ID NO: 36) |
| DDLAF | G30F:<br>CGCCGCTAAGTCGGTCACCGAACCCGACGATCTGGCATTCTAATAG<br>(SEQ ID NO: 37)<br>G30R:<br>CTATTAGAATGCCAGATCGTCGGGTTCGGTGACCGACTTAGCGGCGAT<br>(SEQ ID NO: 38) |

Position 2

| | |
|---|---|
| DDLKA | G4F:<br>CGCCGCTAAGTCGGTCACCGAACCCGACGATCTGAAGGCCTAATAG<br>(SEQ ID NO: 39)<br>G4R:<br>CTATTAGGCCTTCAGATCGTCGGGTTCGGTGACCGACTTAGCGGCGAT<br>(SEQ ID NO: 40) |
| DDLRA | G20F:<br>CGCCGCTAAGTCGGTCACCGAACCCGACGATCTGCGCGCCTAATAG<br>(SEQ ID NO: 41)<br>G20R:<br>CTATTAGGCGCGCAGATCGTCGGGTTCGGTGACCGACTTAGCGGCGAT<br>(SEQ ID NO: 42) |

TABLE 3-continued

Primer pairs used to modify five residues at the C-terminus of modified GFP shown in FIG. 5

| | Primer pair |
|---|---|
| DDLDA | G5F:<br>CGCCGCTAAGTCGGTCACCGAACCCGACGATCTGGACGCCTAATAG<br>(SEQ ID NO: 43)<br>G5R:<br>CTATTAGGCGTCCAGATCGTCGGGTTCGGTGACCGACTTAGCGGCGAT<br>(SEQ ID NO: 44) |
| DDLEA | G19F:<br>CGCCGCTAAGTCGGTCACCGAACCCGACGATCTGGAGGCCTAATAG<br>(SEQ ID NO: 45)<br>G19R:<br>CTATTAGGCCTCCAGATCGTCGGGTTCGGTGACCGACTTAGCGGCGAT<br>(SEQ ID NO: 46) |
| DDLHA | G21F:<br>CGCCGCTAAGTCGGTCACCGAACCCGACGATCTGCACGCCTAATAG<br>(SEQ ID NO: 47)<br>G21R:<br>CTATTAGGCGTGCAGATCGTCGGGTTCGGTGACCGACTTAGCGGCGAT<br>(SEQ ID NO: 48) |
| DDLGA | G28F:<br>CGCCGCTAAGTCGGTCACCGAACCCGACGATCTGGGCGCCTAATAG<br>(SEQ ID NO: 49)<br>G28R:<br>CTATTAGGCGCCCAGATCGTCGGGTTCGGTGACCGACTTAGCGGCGAT<br>(SEQ ID NO: 50) |
| DDLFA | G31F:<br>CGCCGCTAAGTCGGTCACCGAACCCGACGATCTGTTCGCCTAATAG<br>(SEQ ID NO: 51)<br>G31R:<br>CTATTAGGCGAACAGATCGTCGGGTTCGGTGACCGACTTAGCGGCGAT<br>(SEQ ID NO: 52) |

Position 3

| | |
|---|---|
| DDKAA | G6F:<br>CGCCGCTAAGTCGGTCACCGAACCCGACGATAAGGCAGCCTAATAG<br>(SEQ ID NO: 53)<br>G6R:<br>CTATTAGGCTGCCTTATCGTCGGGTTCGGTGACCGACTTAGCGGCGAT<br>(SEQ ID NO: 54) |
| DDRAA | G8F:<br>CGCCGCTAAGTCGGTCACCGAACCCGACGATCGCGCAGCCTAATAG<br>(SEQ ID NO: 55)<br>G8R:<br>CTATTAGGCTGCGCGATCGTCGGGTTCGGTGACCGACTTAGCGGCGAT<br>(SEQ ID NO: 56) |
| DDDAA | G7F:<br>CGCCGCTAAGTCGGTCACCGAACCCGACGATGACGCAGCCTAATAG<br>(SEQ ID NO: 57)<br>G7R:<br>CTATTAGGCTGCGTCATCGTCGGGTTCGGTGACCGACTTAGCGGCGAT<br>(SEQ ID NO: 58) |
| DDEAA | G22F:<br>CGCCGCTAAGTCGGTCACCGAACCCGACGATGAGGCAGCCTAATAG<br>(SEQ ID NO: 59)<br>G22R:<br>CTATTAGGCTGCCTCATCGTCGGGTTCGGTGACCGACTTAGCGGCGAT<br>(SEQ ID NO: 60) |
| DDHAA | G23F:<br>CGCCGCTAAGTCGGTCACCGAACCCGACGATCACGCAGCCTAATAG<br>(SEQ ID NO: 61)<br>G23R:<br>CTATTAGGCTGCGTGATCGTCGGGTTCGGTGACCGACTTAGCGGCGAT<br>(SEQ ID NO: 62) |

TABLE 3-continued

Primer pairs used to modify five residues at the C-terminus of modified GFP shown in FIG. 5

| | Primer pair |
|---|---|
| DDGAA | G29F:<br>CGCCGCTAAGTCGGTCACCGAACCCGACGATGGCGCAGCCTAATAG<br>(SEQ ID NO: 63)<br>G29R:<br>CTATTAGGCTGCGCCATCGTCGGGTTCGGTGACCGACTTAGCGGCGAT<br>(SEQ ID NO: 64) |
| DDFAA | G32F:<br>CGCCGCTAAGTCGGTCACCGAACCCGACGATTTCGCAGCCTAATAG<br>(SEQ ID NO: 65)<br>G32R:<br>CTATTAGGCTGCGAAATCGTCGGGTTCGGTGACCGACTTAGCGGCGAT<br>(SEQ ID NO: 66) |
| Positions 4 and 5 | |
| AALAA | G24F:<br>CGCCGCTAAGTCGGTCACCGAACCCGCCGCCCTGGCAGCCTAATAG<br>(SEQ ID NO: 67)<br>G24R:<br>CTATTAGGCTGCCAGGGCGGCGGGTTCGGTGACCGACTTAGCGGCGAT<br>(SEQ ID NO: 68) |
| KKLAA | G25F:<br>CGCCGCTAAGTCGGTCACCGAACCCAAGAAGCTGGCAGCCTAATAG<br>(SEQ ID NO: 69)<br>G25R:<br>CTATTAGGCTGCCAGCTTCTTGGGTTCGGTGACCGACTTAGCGGCGAT<br>(SEQ ID NO: 70) |
| RRLAA | G26F:<br>CGCCGCTAAGTCGGTCACCGAACCCCGCCGCCTGGCAGCCTAATAG<br>(SEQ ID NO: 71)<br>G26R:<br>CTATTAGGCTGCCAGGCGGCGGGGTTCGGTGACCGACTTAGCGGCGAT<br>(SEQ ID NO: 72) |
| Combination | |
| DDDKD | G9F:<br>CGCCGCTAAGTCGGTCACCGAACCCGACGATGACAAGGACTAATAG<br>(SEQ ID NO: 73)<br>G9R:<br>CTATTAGTCCTTGTCATCGTCGGGTTCGGTGACCGACTTAGCGGCGAT<br>(SEQ ID NO: 74) |

Assay of DesA3

Methods to express DesA3 in *M. smegmatis*, to express Rv3230c in *E. coli*, to prepare cell-free extracts containing these two proteins, and to assay DesA3 activity were as previously reported (Chang and Fox, 2006, *Biochemistry* 45: 13476-13486).

Expression of GFP and Quantification of Fluorescence

*M. smegmatis* was transformed by electroporation, plated onto selective Middlebrook 7H10 agar enriched with Middlebrook OADC (Becton Dickinson, Spark, Md.) containing 50 mg/mL hygromycin, and incubated at 37° C. After 4 days, colonies from each transformation were used to inoculate 500 µL of Middlebrook 7H9 broth (Becton Dickinson, Spark, Md.) supplemented with 0.2% glycerol, 0.05% Tween-80 and 50 mg/mL hygromycin. The liquid cultures were incubated for ~24 h on a shaker (250 rpm) at 37° C. The culture was then diluted 100-fold into 5 mL of fresh liquid medium and grown as before for ~15 h to reach the late logarithmic growth phase. At that time, the culture was induced by addition of anhydrotetracycline to a final concentration of 200 ng/mL for ~6 h with shaking. During this time, fluorescence obtained from the pGFP control plasmid reached a maximum value.

After 6 h, the optical density was measured, and the cells were harvested by centrifugation and washed once in phosphate-buffered saline containing 0.05% Tween20 (PBST) (Sigma-Aldrich, St. Louis, Mo.). The cells were re-suspended in PBST to a density of 2 $OD_{600}$ units per 0.1 mL and re-incubated at 37° C. with shaking. Following this shift back to non-inducing conditions, 0.1 mL samples of the cell culture were transferred into black 384-well plates at various time intervals, and fluorescence was measured using a fluorescence microplate reader (Molecular Devices, Sunnyvale, Calif.) with excitation at 485 nm and detection of emission at 515 nm.

Other Analyses

The alignment of the *M. tuberculosis* DesA3 gene cluster with the genome sequences of other mycobacteria was obtained from the website of The Institute for Genomic Research (TIGR), Rockville, Md.

Influence of C-Terminal on DesA3 Activity

Stearoyl-CoA A $\Delta^9$ desaturase activity could be reconstituted by combining fractions containing DesA3-His6 expressed in *M. smegmatis* with fractions containing Rv3230c expressed in *E. coli* (Chang and Fox, 2006, *Bio-*

*chemistry* 45: 13476-13486). Fractions containing native DesA3 prepared by the same methods had considerably lower catalytic activity. The activity of the following three constructs was compared: DesA3, DesA3-His6 (containing a C-terminal His6 tag), and DesA3-myc (containing a C-terminal myc tag).

FIG. 2 illustrates the effect of adding different C-terminal tags to DesA3 on stearoyl-CoA Δ9 desaturase activity. In FIG. 2, T, S and P correspond to the total (T), supernatant (S), and pellet (P) fractions of lysates prepared from *M. smegmatis* expressing the different DesA3 constructs. The positions of migration of the substrate (18:0), product (18:1) and a side product separated by thin-layer chromatography are indicated. Lanes L1-L3, native DesA3. Lanes L4-L6, DesA3-c-His, containing a C-terminal His6 tag). Lanes L7-L9, DesA3-c-myc, containing a C-terminal myc tag. FIG. 2 shows that native DesA3 had much lower activity, while DesA3-His6 and DesA3-myc showed similar, enhanced activity.

Stability of GFP-DesA3 Fusions in *M. smegmatis*

Figure 3:
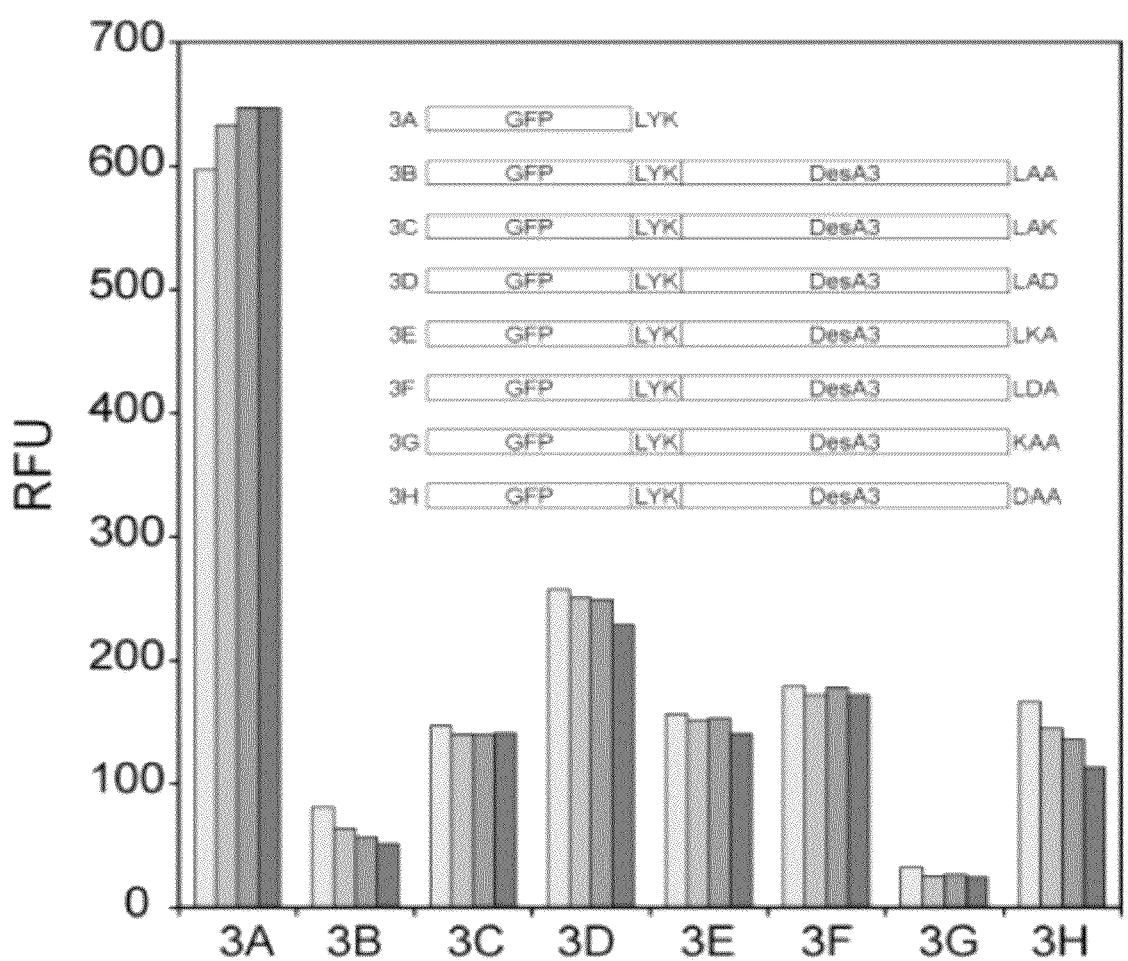
FIG. 3 is a graph showing fluorescence of GFP expressed in *M. smegmatis* and the influence of fusing DesA3 to its C-terminus.

GFP has often been used as a reporter for the expression and stability of expressed fusion proteins (Blokpoel et al., 2003, *J. Microbiol. Methods* 54: 203-211). FIG. 3 shows that GFP, with LYK at the C-terminus (3A), was expressed and was matured to an active form in *M. smegmatis*, and that the induced fluorescence was stable over an ~8 h period after removal of the inducer. Fusion of native DesA3 (~48 kDa) to GFP gave a fusion protein with LAA at the C-terminus (3B), and expression of this fusion protein gave only a low level of fluorescence. In contrast, fusion of variants of DesA3 containing a single lysine or aspartate substitution in the different positions of the LAA sequence (3C to 3G) gave increased GFP fluorescence except for the variant with residues KAA at the C-terminus (3G). For example, the GFP-DesA3-LAD fusion protein (3D) gave ~45% of the fluorescence observed from the unmodified GFP control. Upon consideration that the fusion protein would be an integral membrane protein of ~75 kDa as opposed to the soluble GFP control (~25 kDa), some differences in the overall level of fluorescence were expected. However, the different patterns of protein stability were not expected. The levels of fluorescence and stability observed for the other constructs are shown in FIG. 3.

FIG. 3 illustrates the fluorescence of GFP expressed in *M. smegmatis* and the influence of fusing DesA3 to its C-terminus. The different protein constructs examined in this experiment are shown as the inset, and the three residue sequences shown at the right side of the constructs represent the C-terminus. For example, in 3B, the C-terminus of native DesA3 is LAA. The fluorescence of GFP was measured at t=0, 1, 2, and 4 h after removal of anhydrotetracycline used to induce expression.

GFP-Peptide Fusions

Figure 4:
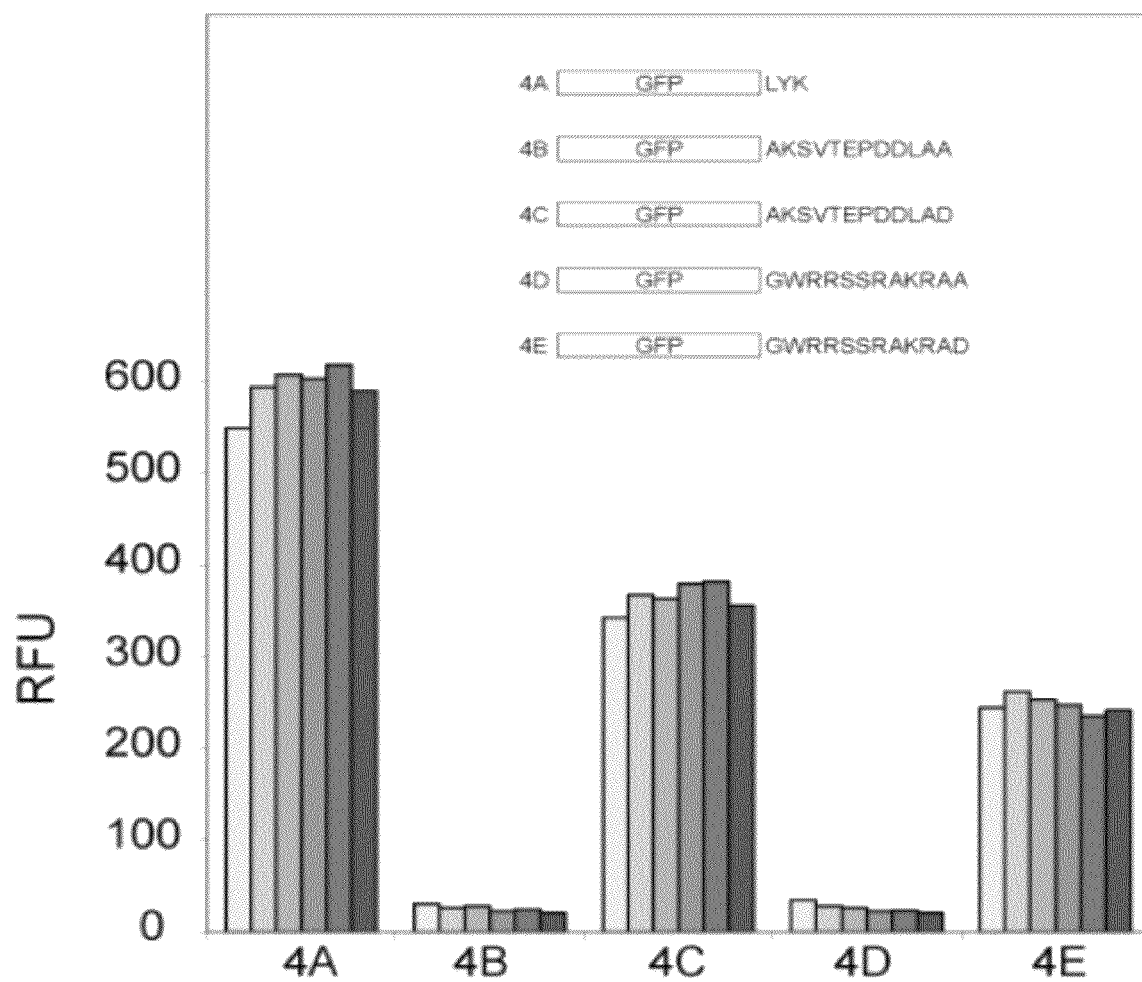
FIG. 4 is a graph showing changes in the intensity and stability of fluorescence when GFP was expressed in *M. smegmatis* with a C-terminal fusion to a 12-residue sequence from DesA3 or the corresponding sequence of the DesA3 homolog from *M. smegmatis*, Msmeg_1886.

In order to address the role of the C-terminus in stability of GFP expressed in *M. smegmatis*, GFP variants with 12 residues added to the C-terminus were studied. The 12 residues came from the C-terminus of native DesA3 or mutated versions of this peptide sequence. FIG. 4 illustrates the changes in the intensity and stability of fluorescence when GFP was expressed in *M. smegmatis* with a C-terminal fusion to a 12-residue sequence from DesA3 or the corresponding sequence of the DesA3 homolog from *M. smegmatis*, Msmeg__1886. A change of the C-terminal Ala residue to Asp increased the level of GFP fluorescence. In common with the results obtained with fusions of the complete integral membrane DesA3, FIG. 4 shows that expression of 4B (containing LAA at the C-terminus) in *M. smegmatis* gave essentially no fluorescence (less than 10% of GFP control, 4A). This loss of fluorescence indicated that 12 residues from the C-terminus of DesA3 were sufficient to stimulate a protein degradation process. In contrast, expression of 4C, where only the C-terminal Ala residue was changed to Asp, gave ~60% of the fluorescence of the control GFP, further supporting the presence of a C-terminal specific protein degradation system. Cells expressing 4C (addition of 12 residues ending in LAD to GFP only) also had somewhat higher fluorescence than cells expressing 3D (a GFP-DesA3 fusion ending in LAD), possibly because the former was better expressed and folded than the latter.

*M. smegmatis* also contains an integral membrane desaturase homolog of DesA3, called Msmeg__1886. When the 12 residues from the C-terminus of Msmeg__1888 were fused to GFP (4D, FIG. 4), stable fluorescence was not observed, while expression of 4E, with the C-terminal Ala mutated to Asp, gave stable fluorescence. Thus *M. smegmatis* also degraded GFP when fused to the C-terminal residues of its own desaturase, suggesting that the process of C-terminal targeted degradation may be conserved for the membrane stearoyl-CoA desaturases in mycobacteria.

Amino Acid Specificity

To further determine the C-terminal sequence preference for this mycobacterial degradation process, the last five residues of the 12-residue C-terminal fusion from DesA3 were systematically varied. Each of the last three residue positions was altered individually, while the fourth and fifth positions from the C-terminus were altered in combination. *M. smegmatis* cells expressing each of the different fusion proteins were measured for GFP fluorescence, and the results are shown in FIG. 5. Illustrated in FIG. 5 is residue specificity of the mycobacterial C-terminally directed degradation/proteolysis system. The fluorescence intensity was monitored over an 8 h period for the GFP-mtX12 variants with each of the last three tail positions altered individually or with the fourth and fifth positions altered together. The last five amino acids of the native DesA3 are DDLAA (SEQ ID NO:77). The amino acid altered at each position is labeled as X. In order to analyze all these variants simultaneously in a time scale that would not be influenced by the observed degradation, a single experiment instead of triplicate experiments was performed. However, similar results were obtained in two other independent experiments.

At position 1 (defined herein as the C-terminal residue, FIG. 5A), GFP variants with charged side chains (Lys, Arg, Asp, Glu and His), large non-polar side chain (Phe), or no side chain (Gly), all exhibited ~50% of the fluorescence observed for the GFP control; notably all exhibited substantially higher fluorescence than GFP with DDLAA (SEQ ID NO:77) at the C-terminus. Most of these variants gave GFP fluorescence that was stable during the time of the experiment, although the Gly and Phe substitutions gave a weak time-dependent loss of fluorescence.

At position 2 (the penultimate amino acid residue, FIG. 5B), GFP variants with the set of investigated residue changes all exhibited higher fluorescence than the GFP with DDLAA (SEQ ID NO:77) at the C-terminus. However, these had markedly different levels of fluorescence and stabilities. Among these, the Glu variant exhibited fluorescence that was equivalent to the GFP positive control and was also stable over the time of the experiment. In contrast, the Phe variant initially exhibited ~50% of the fluorescence of the GFP control but lost ~75% of the fluorescence during the time of the incubation. The remainder of the variants exhibited ~50% of the fluorescence of the GFP control and exhibited only minor changes in fluorescence over time.

At position 3 (the antepenultimate amino acid residue, third residue back from the C terminus, FIG. 5C), only the Gly variant exhibited substantial stable fluorescence. The variants with Asp, Glu, and His exhibited only weak fluorescence and these were unstable during the time of the experiment. Furthermore, variants with basic residues (Arg and Lys) and large non-polar residue (Phe) were comparable to that of GFP with DDLAA (SEQ ID NO:77) at the C-terminus, in that they did not yield fluorescence. In the fourth and fifth positions (FIG. 5D), variants with the substitution of DD to AA, KK, or RR did not stabilize the fluorescence, suggesting that these two positions do not strongly influence the protein degradation process in *M. smegmatis*.

Infrared fluorescence Western blotting

Figure 6:
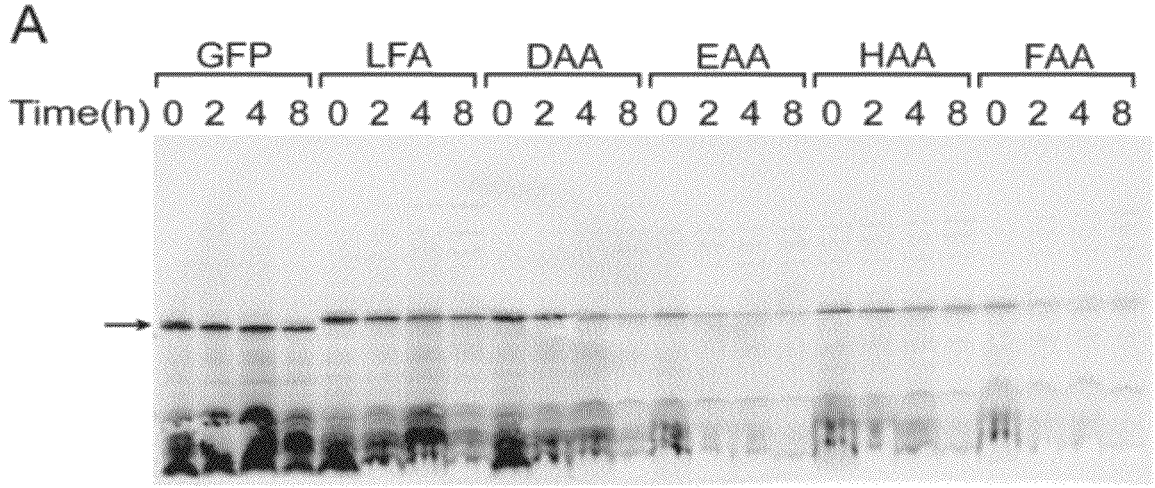
FIG. 6 is an image (A) showing infrared fluorescence Western blot analysis of selected GFP variants, and a table (B) showing the integrated fluorescence intensities of target bands identified in panel A.

In order to distinguish among the alternative possibilities for the origin of decreased GFP fluorescence (e.g., differential protein expression, incorrect protein folding, or protein degradation), quantitative Western blotting using a near-infrared fluorescence detection system was used. The initial fluorescence detected for the GFP control and several labile GFP constructs with modified C-terminal sequences correlated well with the relative protein amount detected by Western blot analysis, suggesting that neither protein expression nor protein folding was the reason for less fluorescence for some variants. Furthermore, FIG. 6 shows that, compared to the GFP control, which had stable fluorescence and detected protein levels, the variants that showed the gradual fluorescence decrease over time also exhibited a correlated decrease in protein detected by Western blotting. This result implicates protein degradation in the loss of fluorescence after the cells were switched to the noninducing conditions.

Combinational Substitution

Figure 7:
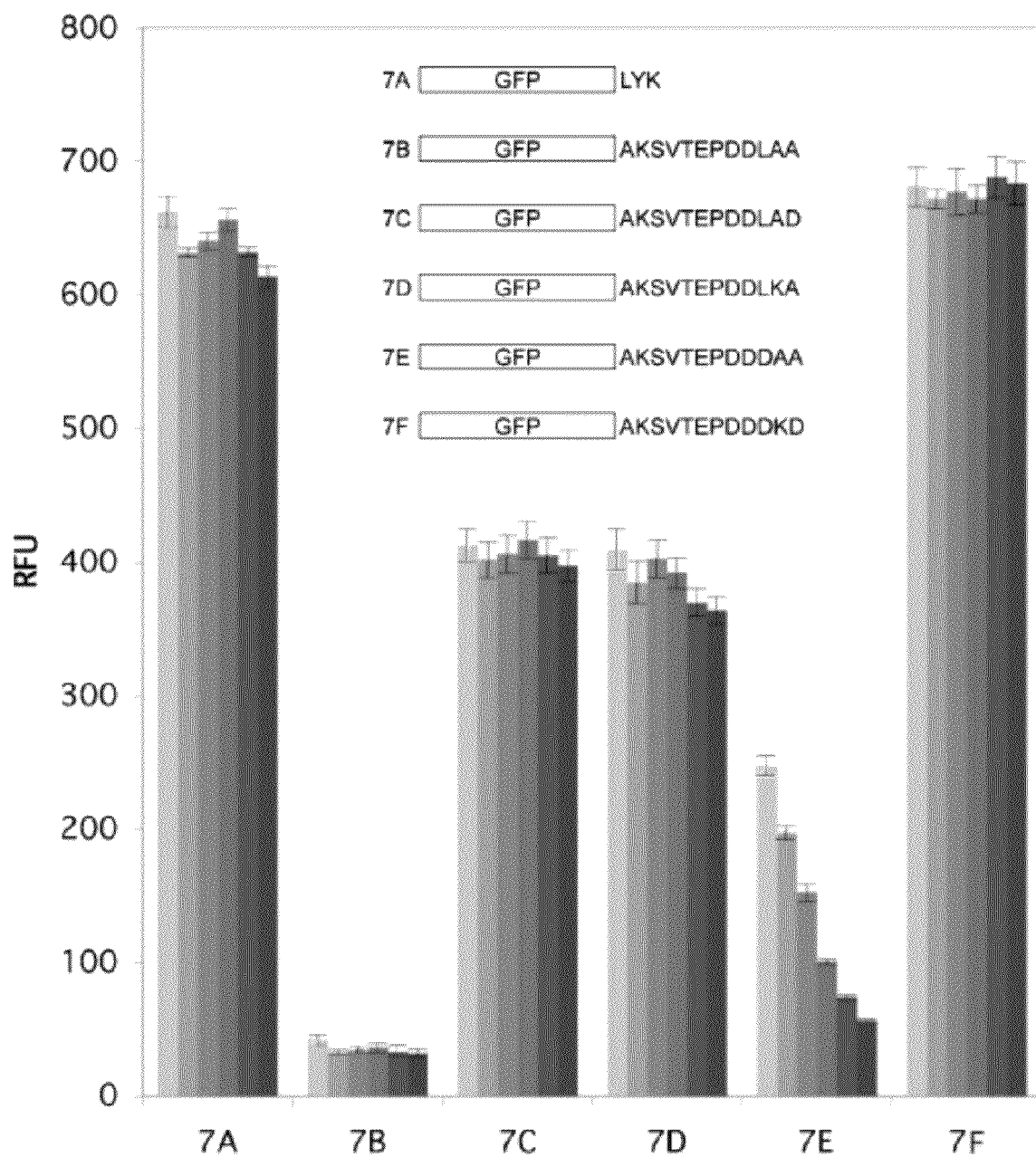
FIG. 7 is a graph showing combinational substitution of residues into the C-terminus of GFP-mtX$_{12}$ variants.

The results of FIGS. 4 and 5 showed that most of the GFP fusions gave only ~50% of the fluorescence of the GFP control, although substitution of Glu alone into the penultimate position gave fluorescence comparable to the GFP control. FIG. 7 shows the combinational substitution of residues into the C-terminus of GFP-mtX12 variants. The fluorescence intensity was monitored over an 8 h period for the GFP-mtX12 variants with each of the last three tail positions altered individually or together. The GFP variant end with DKD (construct 7F) has fluorescence intensity comparable to the GFP positive control.

FIG. 7 shows that combined substitution of DKD for LAA at the C-terminus also gave fluorescence comparable to the GFP control, which was again nearly double that obtained from any of the single substitution variants except the previously mentioned Glu at the second position. Not wanting to be bound by the following theory, these results suggest that the last three positions of the C-terminus may cooperatively determine the specificity of the degradation system, but also that the penultimate position may play a dominant role.

Catalytic Activity of DesA3 C-terminal Variants

Figure 8:
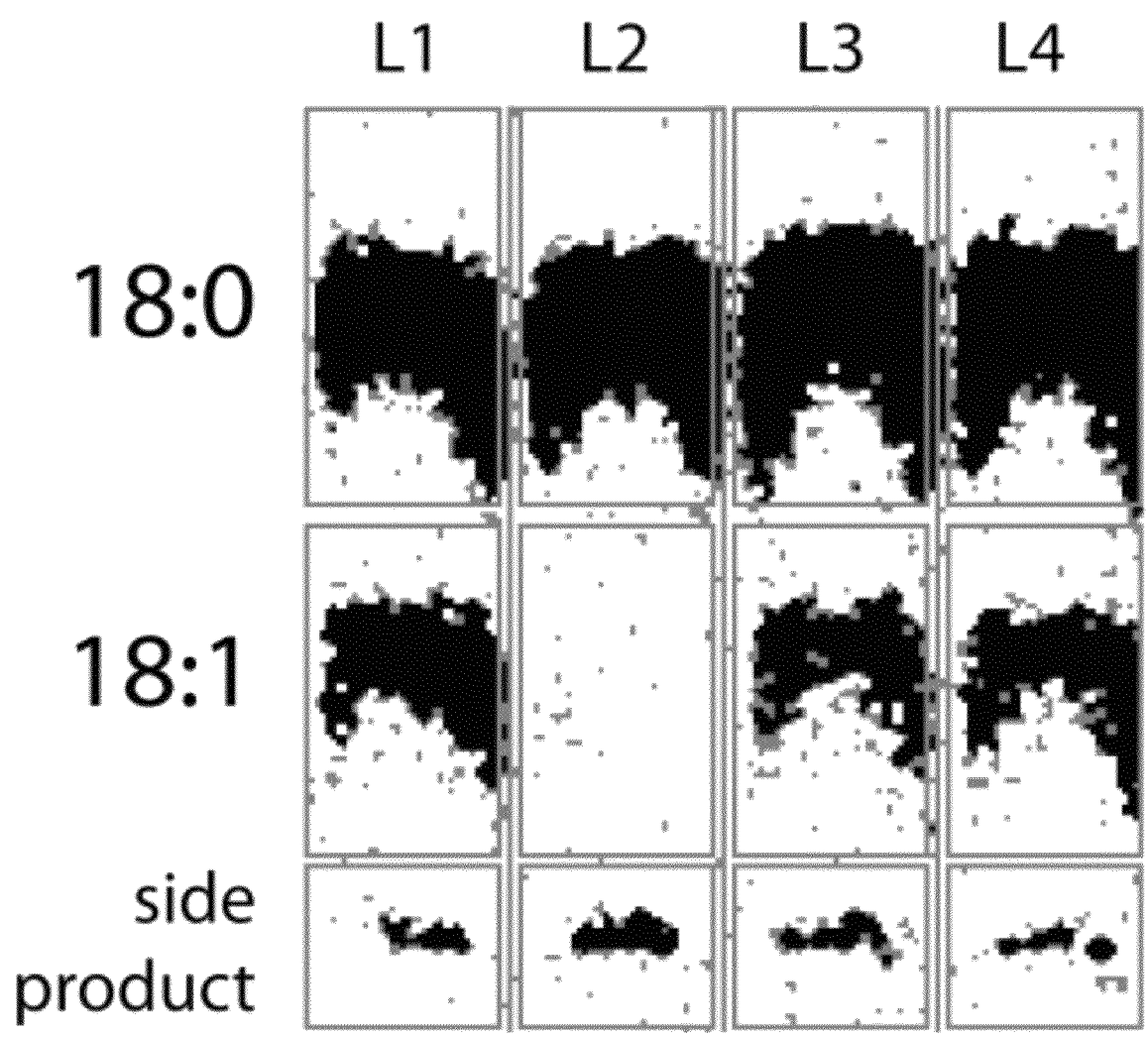
FIG. 8 is an image depicting Stearoyl-CoA Δ9 desaturase activity assays for DesA3 variants expressed in *M. smegmatis*.

FIG. 8 illustrates the stearoyl-CoA Δ9 desaturase activity assays for DesA3 variants expressed in *M. smegmatis*. Lane L1, the total lysate expressing DesA3-myc (containing a C-terminal myc tag). Lane 2, native DesA3-LAA. Lane 3, DesA3-DKD. Lane 4, DesA3-LEA. The positions of migration of the substrate (18:0), product (18:1) and a side product in the thin-layer chromatography separation are indicated.

Preparation of the Cell-Free Lysates and Membrane Fractions takes several hours, so there is substantial opportunity for degradative processes to occur. The activity observed from DesA3 with a C-terminal myc tag (lane L1) was considerably higher than that observed from native DesA3 (lane L2). Since the GFP fusion studies showed that substitution of the last three amino acids from LAA to either DKD or LEA could yield high, stable fluorescence, these changes were made to the last three residues of DesA3. FIG. 8, lanes L3 and L4, show that these changes gave stearoyl-CoA Δ9 desaturase activity comparable to that of the DesA3-c-myc lysate (lane L1), while the activity of the native DesA3 ending in LAA (lane L2) was near completely lost in the time of preparation. Thus the improved fluorescence intensity and stability given by changes made to the GPF fusion proteins corresponded to improved activity of *M. tuberculosis* DesA3 expressed in *M. smegmatis*, presumably by protection of the expressed protein from degradation.

Protein Degradation Systems

Previous studies of the *E. coli* C-terminal targeted protein degradation systems ClpXP and Tsp showed that small and uncharged residues enhanced the degradation. In contrast to the present invention, the several types of C-terminal targeted protein degradation complexes that have previously been identified In *E. coli* have different substrate recognition properties, and different contributions to proteolytic processing.

ClpXP, ClpAP, and Tsp are C-terminal targeted systems with preference for small and uncharged residues (Ala, Cys, Ser, Thr, Val) in last three positions of the protein targeted for degradation, with a few ClpAP substrates identified to alternatively have an N-terminal degradation signal. The ClpXP and ClpAP complexes consist of a hexameric Clp/HSP100 family ATPase, either ClpA or ClpX, and ClpP. ClpP is a serine peptidase whose active site faces an internal chamber. In both ClpXP and ClpAP, the ATPase mediates substrate recognition and catalyzes energy-dependent protein unfolding. The unfolded substrate then translocates through a channel in the hexameric ClpX or ClpA structure into the ClpP chamber for degradation. Both of these systems recognize proteins having a C-terminal SsrA tag (AANDENYALAA; SEQ ID NO:78), which is appended to nascent polypeptide chains that have stalled on bacterial ribosomes by a cotranslational process. Although DesA3 ends with LAA, the adjacent sequence (AKSVTEPDD; SEQ ID NO:79) is not otherwise closely related to the sequence of the SsrA tag.

The ClpXP system is similar to ClpAP in that it recognizes the α-carboxyl group and the C-terminal LAA residues of the SsrA tag as binding determinants. However, ClpXP uses the SspB adaptor protein bound to a secondary site of SsrA tag to enhance recognition of the tagged protein. SspB binding to the SsrA tag inhibits the ClpAP system, pointing to structural differences between these two protease systems. About half of the known natural ClpX substrates are similar to SsrA tagged proteins in that they have nonpolar side chains at the penultimate and C-terminal residues. Moreover, in some sequences, a C-terminal LAA tripeptide is sufficient to allow ClpXP dependent degradation, while substitution of Asp for either of the last two Ala residues completely blocked substrate recognition by ClpX.

FtsH is the only known essential protease in *E. coli*. It is a membrane-anchored protein with its active site in the cytoplasm. FtsH can recognize SsrA tagged proteins and substrates with a C-terminal nonpolar sequence located either in the cytoplasm or the membrane. It has been suggested that the major role of FtsH is to degrade abnormal membrane proteins that have their C-terminal in the cytoplasm, regardless of whether they are SsrA-tagged or not.

The periplasmic endoprotease Tsp cleaves at discrete sites throughout the polypeptide chain. This reaction also depends upon the identity of the substrate's C-terminal sequence and requires the presence of a free α-carboxyl group. Tsp recognizes a relatively apolar C-terminal sequence, for example WVAAA (SEQ ID NO: 80) or LAA, while proteins having a polar C-terminal sequence, for example RSEYE (SEQ ID NO:81) are not cleaved. The identity of the C-terminal residue of this sequence is the most important determinant of the rate of reaction, and small, uncharged residues (Ala, Cys, Ser, Thr, Val) are preferred for proteolytic processing. Furthermore, non-polar residues are preferred at the second and third positions, but larger and more hydrophobic side chains are also acceptable at these positions.

Mycobacterial Protein Degradation System

The presence of a Clp-like protease system was originally proposed for *M. smegmatis* based on biochemical studies (Kim et al., 2000, *Mol. Cell.* 5: 639-648). More recently, the completion of the *M. smegmatis* genome sequence, available at The Institute for Genomic Research website, has made some of the present analysis possible. Thus Msmeg_4671 is annotated as the ClpX homolog, while Msmeg_4672 and Msmeg_4673 are annotated to be the subunits of a dimeric ClpP homolog. In the *M. tuberculosis* genome, these comparable genes are Rv2457c, Rv2460c, and Rv2461c, respectively. *M. smegmatis* contains the chaperonin like ATPase homologs ClpB (Msmeg_0732) and ClpC (Msmeg_6091), while the comparable genes in *M. tuberculosis* are Rv0384c and Rv3596c. *M. smegmatis* contains an additional ClpX isoform (Msmeg_2792) and its homolog in *M. tuberculosis* is Rv2667. Moreover, *M. smegmatis* has an FtsH homolog Msmeg_6105, and the comparable gene in *M. tuberculosis* is Rv3610c. No apparent Tsp homologs have been identified, which may reflect the differences in extracellular structure of mycobacteria as compared to gram-negative bacteria such as *E. coli*.

Not wanting to be bound by the following theory, considering the membrane localization of DesA3, FtsH might reasonably be involved in the control of DesA3 stability. However, the degradation of DesA3 might also be controlled by either of the cytoplasmic Clp systems, as suggested by the facile degradation of soluble GFP fusions shown here.

Specificity of *M. smegmatis* Protein Degradation

By using a set of GFP variants where each of the last five residues of the polypeptide chain was altered, it was discovered that the last three residues had the most influence on the stability of the expressed fusion protein, and that the penultimate residue was individually most influential. No significant improvements in the stabilities of the expressed fusion proteins were observed for the variants with combinational alterations for the fourth and fifth positions.

For expression in *M. smegmatis*, charged side chains (Lys, Arg, Asp, Glu and His), a large non-polar side chain (Phe), or no side chain (Gly) at the C-terminus stabilized the GFP fusion proteins (position 1, FIG. 5A). These classes of residues were also stabilizing at the penultimate amino acid residue (position 2, FIG. 5B), but with the notable exception that the Glu variant had enhanced fluorescence and stability comparable to the GFP control. Placement of Phe at the penultimate position yielded a unique, progressive loss of fluorescence after the inducer was removed. At the third position from the C terminus (FIG. 5C), only the Gly variant exhibited and maintained fluorescence. Other variants at the third position with either acidic or basic side chains (Asp, Glu, His, Arg, and Lys) or Phe exhibited weak fluorescence and this was not stable during the time course of the experiment.

When compared with *E. coli* ClpXP and Tsp systems, the mycobacterial system(s) apparently differs in the relative importance of the last three residues for substrate recognition. Not wanting to be bound by the following theory, the results of FIG. 5 suggest that position 2 may be the strongest single determinant of specificity for the mycobacterial degradation system, while position 1 appears to be the strongest determinant in ClpXP and Tsp. The increased stability observed for the GFP variant with Glu was not replicated with Asp at position 2 (FIG. 5B), which suggests a combination of both charge and size effects in the recognition process.

The results from FIGS. 4 and 5 suggested that a combination of changes from LAA to either LEA or DKD at the C-terminus would promote stability of the GFP fusion protein, and this was indeed true. This result confirms that each of the last three positions of the C-terminus make some contributions to the recognition specificity for the mycobacterial degradation. Moreover, the stability of the GFP control (ends with LYK), DesA3-myc (ends with EDL), and DesA3-His6 can also be explained by the residue preferences and the combinational effects reported here.

*Mycobacterium smegmatis* as an Expression Host

*M. smegmatis* is a non-pathogenic mycobacterium that grows faster than pathogenic mycobacteria and transforms efficiently. It has been often used as an alternative to *E. coli* for heterologous expression, possibly due to the better folding and posttranslational modification of mycobacterial proteins in a phylogenetically related expression host. Shown herein is the use of a tetracycline-inducible vector system that yields reproducible, titratable expression dependent on the concentration of tetracycline added to the culture medium. According to the compositions and methods of the present invention, the stability of other recombinant proteins expressed in *M. smegmatis* might be predicted and possibly improved by consideration of the C-terminal sequence.

Mycobacterial Processing of DesA3

DesA3 is an essential enzyme in fatty acid biosynthesis. Many experiments suggest that DesA3 activity is tightly regulated under laboratory conditions that mimic the different stages of *M. tuberculosis* infection. Since both DesA3 and the *M. smegmatis* homolog Msmeg_1886 have the requisite small residues at their C-termini, a protease degradation mechanism is feasible for controlling the activity of this essential enzyme by post-translational processing.

The rapid post-translational degradation observed for DesA3 and for GFP tagged to the native C-terminal of DesA3 provides new evidence for one mechanism used to control expression of an essential gene in *M. smegmatis*. Since most proteases are conserved among bacteria from the same family, the substrate selectivity rules identified here may be useful to predict protein stability or pathways of proteolytic degradation in *M. tuberculosis* and in other pathogenic mycobacteria. For comparison, the AKSVTEPDDLAA (SEQ ID NO:82) sequence at the end of DesA3 is exactly duplicated in the homologous protein from *Mycobacterium bovis* and is substituted by the SVARRTGGELAA (SEQ ID NO:83) sequence in the *Mycobacterium avium* protein, but still retains the critical LAA terminus.

Other Mycobacterial Degradation Targets

Search of the *M. tuberculosis* H37Rv genome for proteins whose last two residues consisted of any combination of the residues Ala, Cys, Ile, Leu, Ser, Thr, or Val and whose third to the last residue was not Asp, Gly, Glu, or His, revealed 549 examples out of the complete genome of 3918 coding sequences. These may include a subset of proteins and enzymes that have a short lifetime in the cell due to proteolytic processing. Furthermore, only 47 unique patterns of C-terminal peptides were identified out of 784 possible combinations of the specified residues. Not wanting to be bound by the following theory, this indicates that the nature of the residues at the C-terminal is not statistically distributed, but instead possibly represents some bias, perhaps the GC bias of mycobacteria or a functional specialization.

Table 4 shows the subset of the predicted proteolytically regulated proteins from *M. tuberculosis* H37Rv that are also among the ~200 essential genes for survival. There are a number of annotated proteins and enzymes among these 21 proteins, such as membrane transporters, biosynthetic enzymes, and others whose cellular level might reasonably need to be regulated. It is reasonable that DesA3 is among these, given the level of regulation known for the mammalian homolog. Table 4 provides a summary of these proteins and enzymes from M. tuberculosis H37Rv.

TABLE 4

Proteins from M. tuberculosis H37Rv containing C-terminal sequence that may destabilize the protein for proteolytic processing that are also identified as being essential for survival[1]

| Protein[2,3] | Annotation |
| --- | --- |
| Rv1013 | possible polyketide synthase |
| Rv1411c | probable lipoprotein |
| Rv1589 | biotin synthase bioB |
| Rv1653 | glutamate N-acetyltransferase |
| Rv2335 | probable serine acetyltransferase |
| Rv3061c | acyl-CoA dehydrogenase |
| Rv3229c | DesA3 |
| Rv3544c | acyl-CoA dehydrogenase |
| Rv3758c | probable ABC transporter |
| Rv3810 | cell surface protein precursor |

[1]Sassetti and Rubin, 2003, Proc. Natl. Acad. Sci. USA 100: 12989-12994.
[2]Gene identifier from sequenced genome.
[3]Proteins that contain any combination of the residues Ala, Cys, Ile, Leu, Ser, Thr, or Val in the last two positions of the primary sequence and do not contain stabilizing residues Asp, Gly, Glu, or His in the third to the last position. These proteins are predicted to be susceptible to C-terminal directed proteolytic processing. The hypothetical proteins identified are Rv0636, Rv1211, Rv2004c, Rv3087, Rv3277, Rv3335c, Rv3523, Rv3616c, Rv3651, Rv3864, and Rv3910.

Various software programs may be used to evaluate any sequence at the C-terminus of a protein. In one example, the following Python (Python Software Foundation, Hampton, N.H.) files are used to evaluate the C-terminal of proteins in complete genome for amino acid residue sequences that may promote proteolytic processes or stability against processing:
1) 01_readme.txt—A help file describing the required input files and variables for use with ctermseqmatcher.py, ctermseqmatcher_last2.py, and ctermseqmatcher_last2_not3.py;
2) 02_H37Rv_proteome.txt—a text file in FASTA format that contains the protein sequences of interest. This file contains the complete proteome of Mycobacterium tuberculosis H37Rv. Other genomes in the same format can be analyzed by these routines;
3) 03_EssentailgeneinfectionTable3.csv2—A comma separated values file containing a list of protein sequences of interest. In this case, the file contains information on proteins identified to be essential for the viability of Mycobacterium tuberculosis. The second column of the file must contain a gene identifier tag in the format Rv#####, as used in the designation of genes in the Mycobacterium tuberculosis H37Rv genome;
4) 04_ctermseqmatcher.py—routine to investigate frequency of specific tripeptide sequences at the end of a protein sequence;
5) 05_ctermseqmatcher_total_last2_not3.py—A program to select all proteins that have the desired C-terminal sequence in the Mycobacterium tuberculosis H37Rv genome;
6) 06_ctermseqmatcher_select_last2_not3.py—A program to select all proteins that have the desired C-terminal sequence in the Mycobacterium tuberculosis H37Rv genome and that are also found in the EssentailgeneinfectionTable3.csv2 file;
7) 07_ctermseqmatcher_totallast2.py—A program that selects the all proteins with two-residue C-terminal sequence that defines the most stable subset of proteins in Mycobacterium tuberculosis;
8) 08_ctermseqmatcher_select_last2.py—A program that selects the all proteins with two-residue C-terminal sequence that defines the most stable subset of proteins in Mycobacterium tuberculosis that are also found in the EssentailgeneinfectionTable3.csv2 file;
9) 09_AVSTC$_1$_GDEH_Total.txt—Output of ctermseqmatcher_select_last2.py. The set of predicted least stable proteins from Mycobacterium tuberculosis H37Rv genome based on C-terminal sequence where the last two residues are from the set of residues AVSTCLI and the third to the last residue cannot be GDEH;
10) 10_AVSTCLI_GDEH_Select.txt—Output of ctermseqmatcher_select_last2.py. The set of predicted least stable proteins from Mycobacterium tuberculosis H37Rv genome and from the list of essential genes based on C-terminal sequence where the last two residues are from the set of residues AVSTCLI and the third to the last residue cannot be GDEH;
11) 11_hits2_KRDEHFGWYP_Total.txt—Output of ctermseqmatcher_select_last2_not3.py. Set of predicted most stable proteins from Mycobacterium tuberculosis H37Rv genome.
12) 12_hits2_KRDEHFGWYP_Select.txt—Output of ctermseqmatcher_select_last2_not3.py. Set of predicted most stable proteins from Mycobacterium tuberculosis H37Rv genome and from the essential genes list based on C-terminal sequence.

Table 5 is an example of an output Python file, which illustrates a set of predicted most stable proteins from Mycobacterium tuberculosis H37Rv genome based on C-terminal sequence (Chang, et al., 2008, J. Bacteriol. 190: 6686-6694). For example, as shown in Table 5 and footnote 3, the sequence FR found in C-terminus of the gene annotated as Rv1821 (or MTCY1A11.22c), which encodes a possible translocase secA, len: 808, similar to SECA_BACSU P28366 preprotein translocase seca subunit (841 aa), FASTA scores, opt: 1424, z-score:1595.5, E( ): 0, (35.9% identity in 786 aa overlap) (secA2) is one of the predicted most stable proteins in the genome of Mycobacterium tuberculosis. The translocase secA is an essential part of a multiprotein complex that is required to move other proteins produced in the interior of the cell into the cell membrane or across the cell membrane into the extracellular space. The FASTA scores and 35.9% identity of primary sequence in 786 aa (amino acid) overlap indicate a high probability for the correctness of the annotation of the mycobacterial protein. Mycobacteria have many distinct properties of the cell membrane and the extracellular space that contribute to their pathogenicity. By association, the information about the most stable proteins in Mycobacterium tuberculosis may help in the discovery of the most abundant and important proteins required for persistence of the pathogen. These proteins may be important drug targets.

Table 5 shows that a variety of proteins can be identified, which meet criteria for stabilization against C-terminal proteolysis. Footnote 4 of Table 5 shows the Python script ctermseqmatcher_select_last2.py used to identify proteins found in Table 5. Footnote 5 of Table 5 shows the complete Python output from searching the Mycobacterium tuberculosis H37Rv genome and the EssentailgeneinfectionTable3.csv2 file. With understanding of the specificity of C-terminal directed proteolysis, it should be possible to perform similar predictive studies in other microbial species, both pathogenic and beneficial. Thus, in silico screens of any desired protein databases may be performed in order to predict the stability of expressed proteins based on the sequences of their carboxy termini.

TABLE 5

Proteins from *M. tuberculosis* H37Rv containing C-terminal sequence that may stabilize the protein against proteolytic processing that are also identified as being essential for survival[1]

| Protein[2,3,4] | Annotation |
| --- | --- |
| Rv0099 | ligase most similar to long chain fatty acid-CoA ligase |
| Rv0470c | cyclopropane mycolic acid synthase |
| Rv1028c | probable sensor protein |
| Rv1185c | fadD21, acyl-CoA synthase |
| Rv1236 | membrane protein probably involve in sugar transport |
| Rv1237 | sugar (maltose) transporter |
| Rv1244 | unknown lipoprotein |
| Rv1304 | ATP synthase A chain |
| Rv1569 | 8-amino-7-oxononanoate synthase |
| Rv1640c | similarity to lysyl-tRNA synthetase |
| Rv1821 | translocase secA |
| Rv2048c | polyketide synthase |
| Rv2072c | CobL methyl transferase |
| Rv2231 | CobC aminotransferase |
| Rv2937 | daunorubicin resistance transmembrane protein |
| Rv2942 | mmpL1 conserved membrane protein |
| Rv3246c | mtrA response regulator |
| Rv3270 | cation transport ATPase |
| Rv3499c | mce protein family |
| Rv3560c | acyl-CoA dehydrogenase |
| Rv3873 | PPE family |

[1]Sassetti and Rubin, 2003, *Proc. Natl. Acad. Sci. USA* 100: 12989-12994).
[2]Gene identifier from the sequenced genome.
[3]Proteins that contain any combination of the residues Arg, Asp, Gly, Glu, His, Lys, Phe, Pro, Trp or Tyr in the last two positions of the primary sequence. These proteins are predicted to be stabilized against C-terminal directed proteolytic processing. The hypothetical proteins identified are Rv0100, Rv0176, Rv0204c, Rv0218, Rv0566c, Rv0687, Rv1128c, Rv1144, Rv1183, Rv1184c, Rv1405c, Rv1422, Rv1560, Rv1710, Rv1930c, Rv2038c, Rv2277c, Rv2696c, Rv2808, Rv3168, Rv3178, Rv3371, Rv3542c, Rv3614c, Rv3631, Rv3723, Rv3805c, Rv3868, Rv3876, Rv3877 and Rv3882c.
[4]Python script ctermseqmatcher_select_last2.py used to recover information used to prepare Table 5.

It is to be understood that this invention is not limited to the particular devices, methodology, protocols, subjects, or reagents described, and as such may vary. It is also to be understood that the terminology used herein is for the purpose of describing particular embodiments only, and is not intended to limit the scope of the present invention, which is limited only by the claims. Other suitable modifications and adaptations of a variety of conditions and parameters, obvious to those skilled in the art of biochemistry, molecular biology, and bioinformatics, are within the scope of this invention. All publications, patents, and patent applications cited herein are incorporated by reference in their entirety for all purposes.

---

What is claimed is:

1. A method for increasing the stability of a polypeptide, wherein the last two amino acid residues of the carboxy terminal sequence of the polypeptide are independently selected from Ala, Cys, Ile, Leu, Ser, Thr, and Val, and wherein the antepenultimate amino acid residue of the carboxy terminal sequence of the polypeptide is not Asp, Gly, Glu or His, against degradation by a C-terminal specific mycobacterium protease, comprising the step of altering one or more of the last three amino acid residues at the carboxy terminus of the polypeptide, wherein the alteration is selected from the group consisting of amino acid substitution, amino acid insertion, and amino acid deletion, and wherein the alteration results in at least one of:

(a) one or both of the last two amino acid residues of the carboxy terminal sequence of the polypeptide being selected from the group consisting of Arg, Asp, Glu, Gly, His, Lys, Phe, Pro, Trp, and Tyr, and (b) the antepenultimate residue of the carboxy terminal sequence of the polypeptide being selected from the group consisting of Asp, Gly, Glu, and His; and measuring the stability of the altered polypeptide against degradation by the C-terminal specific mycobacterium protease, whereby the stability of the altered polypeptide against degradation by the C-terminal specific mycobacterium protease is increased as compared to the unaltered polypeptide.

2. The method of claim 1 wherein the alteration results in the sequence Asp-Lys-Asp, Leu-Glu-Ala, Leu-Lys-Ala, or Leu-Ala-Asp for the last three amino acid residues at the carboxy terminus of the polypeptide.

3. The method of claim 1, wherein the last three amino acid residues of the carboxy terminal sequence of the polypeptide before the polypeptide is altered are Leu-Ala-Ala.

* * * * *

UNITED STATES PATENT AND TRADEMARK OFFICE
CERTIFICATE OF CORRECTION

PATENT NO.      : 8,268,581 B2
APPLICATION NO. : 12/431315
DATED           : September 18, 2012
INVENTOR(S)     : Brian G. Fox et al.

It is certified that error appears in the above-identified patent and that said Letters Patent is hereby corrected as shown below:

Cover Page, left column, (75) Inventors: lines 2-3, "Gary A. Wesenberg" should be
-- Gary E. Wesenberg --

Column 11, line 42, "Gln (O)" should be -- Gln (Q) --

Signed and Sealed this
Fourth Day of December, 2012

David J. Kappos
*Director of the United States Patent and Trademark Office*

SEQUENCE LISTING

```
<160> NUMBER OF SEQ ID NOS: 83

<210> SEQ ID NO 1
<211> LENGTH: 41
<212> TYPE: DNA
<213> ORGANISM: Artificial Sequence
<220> FEATURE:
<223> OTHER INFORMATION: Native DesA3 5' primer

<400> SEQUENCE: 1
gggaattcca tatggcgatc actgacgtcg acgtattcgc g            41

<210> SEQ ID NO 2
<211> LENGTH: 35
<212> TYPE: DNA
<213> ORGANISM: Artificial Sequence
<220> FEATURE:
<223> OTHER INFORMATION: Native DesA3 3' primer

<400> SEQUENCE: 2
cccaagcttt taggctgcca gatcgtcggg ttcgg                   35

<210> SEQ ID NO 3
<211> LENGTH: 41
<212> TYPE: DNA
<213> ORGANISM: Artificial Sequence
<220> FEATURE:
<223> OTHER INFORMATION: DesA3-His6 5' primer

<400> SEQUENCE: 3
gggaattcca tatggcgatc actgacgtcg acgtattcgc g            41

<210> SEQ ID NO 4
<211> LENGTH: 32
```

```
<212> TYPE: DNA
<213> ORGANISM: Artificial Sequence
<220> FEATURE:
<223> OTHER INFORMATION: DesA3-His6 3' primer

<400> SEQUENCE: 4
cccaagcttg gctgccagat cgtcgggttc gg                              32

<210> SEQ ID NO 5
<211> LENGTH: 41
<212> TYPE: DNA
<213> ORGANISM: Artificial Sequence
<220> FEATURE:
<223> OTHER INFORMATION: DesA3-c-myc 5' primer

<400> SEQUENCE: 5
gggaattcca tatggcgatc actgacgtcg acgtattcgc g                    41

<210> SEQ ID NO 6
<211> LENGTH: 32
<212> TYPE: DNA
<213> ORGANISM: Artificial Sequence
<220> FEATURE:
<223> OTHER INFORMATION: DesA3-c-myc 3' primer

<400> SEQUENCE: 6
cccaagcttg gctgccagat cgtcgggttc gg                              32

<210> SEQ ID NO 7
<211> LENGTH: 41
<212> TYPE: DNA
<213> ORGANISM: Artificial Sequence
<220> FEATURE:
<223> OTHER INFORMATION: DesA3-DKD 5' primer

<400> SEQUENCE: 7
gggaattcca tatggcgatc actgacgtcg acgtattcgc g                    41

<210> SEQ ID NO 8
<211> LENGTH: 39
<212> TYPE: DNA
<213> ORGANISM: Artificial Sequence
<220> FEATURE:
<223> OTHER INFORMATION: DesA3-DKD 3' primer

<400> SEQUENCE: 8
caagctttta gtccttgtca tcgtcgggtt cggtgaccg                       39

<210> SEQ ID NO 9
<211> LENGTH: 41
<212> TYPE: DNA
<213> ORGANISM: Artificial Sequence
<220> FEATURE:
<223> OTHER INFORMATION: DesA3-LEA 5' primer

<400> SEQUENCE: 9
gggaattcca tatggcgatc actgacgtcg acgtattcgc g                    41

<210> SEQ ID NO 10
<211> LENGTH: 39
<212> TYPE: DNA
<213> ORGANISM: Artificial Sequence
<220> FEATURE:
<223> OTHER INFORMATION: DesA3-LEA 3' primer

<400> SEQUENCE: 10
caagctttta ggcctccaga tcgtcgggtt cggtgaccg                       39
```

```
<210> SEQ ID NO 11
<211> LENGTH: 33
<212> TYPE: DNA
<213> ORGANISM: Artificial Sequence
<220> FEATURE:
<223> OTHER INFORMATION: GFP-DesA3 5' primer

<400> SEQUENCE: 11
cccgcgatcg ccatggcgat cactgacgtc gac                                   33

<210> SEQ ID NO 12
<211> LENGTH: 37
<212> TYPE: DNA
<213> ORGANISM: Artificial Sequence
<220> FEATURE:
<223> OTHER INFORMATION: GFP-DesA3 3' primer

<400> SEQUENCE: 12
taatttaaat ctattaggct gccagatcgt cgggttc                               37

<210> SEQ ID NO 13
<211> LENGTH: 39
<212> TYPE: DNA
<213> ORGANISM: Artificial Sequence
<220> FEATURE:
<223> OTHER INFORMATION: GFP-DesA3-LAK 3' primer

<400> SEQUENCE: 13
taatttaaat ctattacttt gccagatcgt cgggttcgg                             39

<210> SEQ ID NO 14
<211> LENGTH: 39
<212> TYPE: DNA
<213> ORGANISM: Artificial Sequence
<220> FEATURE:
<223> OTHER INFORMATION: GFP-DesA3-LAD 3' primer

<400> SEQUENCE: 14
taatttaaat ctattagtct gccagatcgt cgggttcgg                             39

<210> SEQ ID NO 15
<211> LENGTH: 45
<212> TYPE: DNA
<213> ORGANISM: Artificial Sequence
<220> FEATURE:
<223> OTHER INFORMATION: GFP-DesA3-LKA 3' primer

<400> SEQUENCE: 15
taatttaaat ctattaggcc ttcagatcgt cgggttcggt gaccg                      45

<210> SEQ ID NO 16
<211> LENGTH: 44
<212> TYPE: DNA
<213> ORGANISM: Artificial Sequence
<220> FEATURE:
<223> OTHER INFORMATION: GFP-DesA3-LDA 3' primer

<400> SEQUENCE: 16
aatttaaatc tattaggcgt ccagatcgtc gggttcggtg accg                       44

<210> SEQ ID NO 17
<211> LENGTH: 47
<212> TYPE: DNA
<213> ORGANISM: Artificial Sequence
<220> FEATURE:
<223> OTHER INFORMATION: GFP-DesA3-KAA 3' primer
```

```
<400> SEQUENCE: 17
taatttaaat ctattaggct gccttatcgt cgggttcggt gaccgac        47

<210> SEQ ID NO 18
<211> LENGTH: 47
<212> TYPE: DNA
<213> ORGANISM: Artificial Sequence
<220> FEATURE:
<223> OTHER INFORMATION: GFP-DesA3-DAA 3' primer

<400> SEQUENCE: 18
taatttaaat ctattaggct gcgtcatcgt cgggttcggt gaccgac        47

<210> SEQ ID NO 19
<211> LENGTH: 46
<212> TYPE: DNA
<213> ORGANISM: Artificial Sequence
<220> FEATURE:
<223> OTHER INFORMATION: G1F primer

<400> SEQUENCE: 19
cgccgctaag tcggtcaccg aacccgacga tctggcagcc taatag         46

<210> SEQ ID NO 20
<211> LENGTH: 48
<212> TYPE: DNA
<213> ORGANISM: Artificial Sequence
<220> FEATURE:
<223> OTHER INFORMATION: G1R primer

<400> SEQUENCE: 20
ctattaggct gccagatcgt cgggttcggt gaccgactta gcggcgat       48

<210> SEQ ID NO 21
<211> LENGTH: 46
<212> TYPE: DNA
<213> ORGANISM: Artificial Sequence
<220> FEATURE:
<223> OTHER INFORMATION: G11F primer

<400> SEQUENCE: 21
cgccggctgg cgccggtcga gccgggccaa gcgcgccgcc tagtaa         46

<210> SEQ ID NO 22
<211> LENGTH: 48
<212> TYPE: DNA
<213> ORGANISM: Artificial Sequence
<220> FEATURE:
<223> OTHER INFORMATION: G11R primer

<400> SEQUENCE: 22
ttactaggcg gcgcgcttgg cccggctcga ccggcgccag ccggcgat       48

<210> SEQ ID NO 23
<211> LENGTH: 46
<212> TYPE: DNA
<213> ORGANISM: Artificial Sequence
<220> FEATURE:
<223> OTHER INFORMATION: G12F primer

<400> SEQUENCE: 23
cgccggctgg cgccggtcga gccgggccaa gcgcgccgac tagtaa         46

<210> SEQ ID NO 24
<211> LENGTH: 48
```

```
<212> TYPE: DNA
<213> ORGANISM: Artificial Sequence
<220> FEATURE:
<223> OTHER INFORMATION: G12R primer

<400> SEQUENCE: 24
ttactagtcg gcgcgcttgg cccggctcga ccggcgccag ccggcgat          48

<210> SEQ ID NO 25
<211> LENGTH: 46
<212> TYPE: DNA
<213> ORGANISM: Artificial Sequence
<220> FEATURE:
<223> OTHER INFORMATION: G2F primer

<400> SEQUENCE: 25
cgccgctaag tcggtcaccg aacccgacga tctggcaaag taatag            46

<210> SEQ ID NO 26
<211> LENGTH: 48
<212> TYPE: DNA
<213> ORGANISM: Artificial Sequence
<220> FEATURE:
<223> OTHER INFORMATION: G2R primer

<400> SEQUENCE: 26
ctattacttt gccagatcgt cgggttcggt gaccgactta gcggcgat          48

<210> SEQ ID NO 27
<211> LENGTH: 46
<212> TYPE: DNA
<213> ORGANISM: Artificial Sequence
<220> FEATURE:
<223> OTHER INFORMATION: G17F primer

<400> SEQUENCE: 27
cgccgctaag tcggtcaccg aacccgacga tctggcacgc taatag            46

<210> SEQ ID NO 28
<211> LENGTH: 48
<212> TYPE: DNA
<213> ORGANISM: Artificial Sequence
<220> FEATURE:
<223> OTHER INFORMATION: G17R primer

<400> SEQUENCE: 28
ctattagcgt gccagatcgt cgggttcggt gaccgactta gcggcgat          48

<210> SEQ ID NO 29
<211> LENGTH: 46
<212> TYPE: DNA
<213> ORGANISM: Artificial Sequence
<220> FEATURE:
<223> OTHER INFORMATION: G3F primer

<400> SEQUENCE: 29
cgccgctaag tcggtcaccg aacccgacga tctggcagac taatag            46

<210> SEQ ID NO 30
<211> LENGTH: 48
<212> TYPE: DNA
<213> ORGANISM: Artificial Sequence
<220> FEATURE:
<223> OTHER INFORMATION: G3R primer

<400> SEQUENCE: 30
ctattagtct gccagatcgt cgggttcggt gaccgactta gcggcgat          48
```

```
<210> SEQ ID NO 31
<211> LENGTH: 46
<212> TYPE: DNA
<213> ORGANISM: Artificial Sequence
<220> FEATURE:
<223> OTHER INFORMATION: G16F primer

<400> SEQUENCE: 31
cgccgctaag tcggtcaccg aacccgacga tctggcagag taatag          46

<210> SEQ ID NO 32
<211> LENGTH: 48
<212> TYPE: DNA
<213> ORGANISM: Artificial Sequence
<220> FEATURE:
<223> OTHER INFORMATION: G16R primer

<400> SEQUENCE: 32
ctattactct gccagatcgt cgggttcggt gaccgactta gcggcgat          48

<210> SEQ ID NO 33
<211> LENGTH: 46
<212> TYPE: DNA
<213> ORGANISM: Artificial Sequence
<220> FEATURE:
<223> OTHER INFORMATION: G18F primer

<400> SEQUENCE: 33
cgccgctaag tcggtcaccg aacccgacga tctggcacac taatag          46

<210> SEQ ID NO 34
<211> LENGTH: 48
<212> TYPE: DNA
<213> ORGANISM: Artificial Sequence
<220> FEATURE:
<223> OTHER INFORMATION: G18R primer

<400> SEQUENCE: 34
ctattagtgt gccagatcgt cgggttcggt gaccgactta gcggcgat          48

<210> SEQ ID NO 35
<211> LENGTH: 46
<212> TYPE: DNA
<213> ORGANISM: Artificial Sequence
<220> FEATURE:
<223> OTHER INFORMATION: G27F primer

<400> SEQUENCE: 35
cgccgctaag tcggtcaccg aacccgacga tctggcaggc taatag          46

<210> SEQ ID NO 36
<211> LENGTH: 48
<212> TYPE: DNA
<213> ORGANISM: Artificial Sequence
<220> FEATURE:
<223> OTHER INFORMATION: G27R primer

<400> SEQUENCE: 36
ctattagcct gccagatcgt cgggttcggt gaccgactta gcggcgat          48

<210> SEQ ID NO 37
<211> LENGTH: 46
<212> TYPE: DNA
<213> ORGANISM: Artificial Sequence
<220> FEATURE:
<223> OTHER INFORMATION: G30F primer
```

-continued

<400> SEQUENCE: 37
cgccgctaag tcggtcaccg aacccgacga tctggcattc taatag    46

<210> SEQ ID NO 38
<211> LENGTH: 48
<212> TYPE: DNA
<213> ORGANISM: Artificial Sequence
<220> FEATURE:
<223> OTHER INFORMATION: G30R primer

<400> SEQUENCE: 38
ctattagaat gccagatcgt cgggttcggt gaccgactta gcggcgat    48

<210> SEQ ID NO 39
<211> LENGTH: 46
<212> TYPE: DNA
<213> ORGANISM: Artificial Sequence
<220> FEATURE:
<223> OTHER INFORMATION: G4F primer

<400> SEQUENCE: 39
cgccgctaag tcggtcaccg aacccgacga tctgaaggcc taatag    46

<210> SEQ ID NO 40
<211> LENGTH: 48
<212> TYPE: DNA
<213> ORGANISM: Artificial Sequence
<220> FEATURE:
<223> OTHER INFORMATION: G4R primer

<400> SEQUENCE: 40
ctattaggcc ttcagatcgt cgggttcggt gaccgactta gcggcgat    48

<210> SEQ ID NO 41
<211> LENGTH: 46
<212> TYPE: DNA
<213> ORGANISM: Artificial Sequence
<220> FEATURE:
<223> OTHER INFORMATION: G20F primer

<400> SEQUENCE: 41
cgccgctaag tcggtcaccg aacccgacga tctgcgcgcc taatag    46

<210> SEQ ID NO 42
<211> LENGTH: 48
<212> TYPE: DNA
<213> ORGANISM: Artificial Sequence
<220> FEATURE:
<223> OTHER INFORMATION: G20R primer

<400> SEQUENCE: 42
ctattaggcg cgcagatcgt cgggttcggt gaccgactta gcggcgat    48

<210> SEQ ID NO 43
<211> LENGTH: 46
<212> TYPE: DNA
<213> ORGANISM: Artificial Sequence
<220> FEATURE:
<223> OTHER INFORMATION: G5F primer

<400> SEQUENCE: 43
cgccgctaag tcggtcaccg aacccgacga tctggacgcc taatag    46

<210> SEQ ID NO 44
<211> LENGTH: 48

```
<212> TYPE: DNA
<213> ORGANISM: Artificial Sequence
<220> FEATURE:
<223> OTHER INFORMATION: G5R primer

<400> SEQUENCE: 44
ctattaggcg tccagatcgt cgggttcggt gaccgactta gcggcgat            48

<210> SEQ ID NO 45
<211> LENGTH: 46
<212> TYPE: DNA
<213> ORGANISM: Artificial Sequence
<220> FEATURE:
<223> OTHER INFORMATION: G19F primer

<400> SEQUENCE: 45
cgccgctaag tcggtcaccg aacccgacga tctggaggcc taatag              46

<210> SEQ ID NO 46
<211> LENGTH: 48
<212> TYPE: DNA
<213> ORGANISM: Artificial Sequence
<220> FEATURE:
<223> OTHER INFORMATION: G19R primer

<400> SEQUENCE: 46
ctattaggcc tccagatcgt cgggttcggt gaccgactta gcggcgat            48

<210> SEQ ID NO 47
<211> LENGTH: 46
<212> TYPE: DNA
<213> ORGANISM: Artificial Sequence
<220> FEATURE:
<223> OTHER INFORMATION: G21F primer

<400> SEQUENCE: 47
cgccgctaag tcggtcaccg aacccgacga tctgcacgcc taatag              46

<210> SEQ ID NO 48
<211> LENGTH: 48
<212> TYPE: DNA
<213> ORGANISM: Artificial Sequence
<220> FEATURE:
<223> OTHER INFORMATION: G21R primer

<400> SEQUENCE: 48
ctattaggcg tgcagatcgt cgggttcggt gaccgactta gcggcgat            48

<210> SEQ ID NO 49
<211> LENGTH: 46
<212> TYPE: DNA
<213> ORGANISM: Artificial Sequence
<220> FEATURE:
<223> OTHER INFORMATION: G28F primer

<400> SEQUENCE: 49
cgccgctaag tcggtcaccg aacccgacga tctgggcgcc taatag              46

<210> SEQ ID NO 50
<211> LENGTH: 48
<212> TYPE: DNA
<213> ORGANISM: Artificial Sequence
<220> FEATURE:
<223> OTHER INFORMATION: G28R primer

<400> SEQUENCE: 50
ctattaggcg cccagatcgt cgggttcggt gaccgactta gcggcgat            48
```

<210> SEQ ID NO 51
<211> LENGTH: 46
<212> TYPE: DNA
<213> ORGANISM: Artificial Sequence
<220> FEATURE:
<223> OTHER INFORMATION: G31F primer

<400> SEQUENCE: 51
cgccgctaag tcggtcaccg aacccgacga tctgttcgcc taatag                46

<210> SEQ ID NO 52
<211> LENGTH: 48
<212> TYPE: DNA
<213> ORGANISM: Artificial Sequence
<220> FEATURE:
<223> OTHER INFORMATION: G31R primer

<400> SEQUENCE: 52
ctattaggcg aacagatcgt cgggttcggt gaccgactta gcggcgat              48

<210> SEQ ID NO 53
<211> LENGTH: 46
<212> TYPE: DNA
<213> ORGANISM: Artificial Sequence
<220> FEATURE:
<223> OTHER INFORMATION: G6F primer

<400> SEQUENCE: 53
cgccgctaag tcggtcaccg aacccgacga taaggcagcc taatag                46

<210> SEQ ID NO 54
<211> LENGTH: 48
<212> TYPE: DNA
<213> ORGANISM: Artificial Sequence
<220> FEATURE:
<223> OTHER INFORMATION: G6R primer

<400> SEQUENCE: 54
ctattaggct gccttatcgt cgggttcggt gaccgactta gcggcgat              48

<210> SEQ ID NO 55
<211> LENGTH: 46
<212> TYPE: DNA
<213> ORGANISM: Artificial Sequence
<220> FEATURE:
<223> OTHER INFORMATION: G8F primer

<400> SEQUENCE: 55
cgccgctaag tcggtcaccg aacccgacga tcgcgcagcc taatag                46

<210> SEQ ID NO 56
<211> LENGTH: 48
<212> TYPE: DNA
<213> ORGANISM: Artificial Sequence
<220> FEATURE:
<223> OTHER INFORMATION: G8R primer

<400> SEQUENCE: 56
ctattaggct gcgcgatcgt cgggttcggt gaccgactta gcggcgat              48

<210> SEQ ID NO 57
<211> LENGTH: 46
<212> TYPE: DNA
<213> ORGANISM: Artificial Sequence
<220> FEATURE:
<223> OTHER INFORMATION: G7F primer

```
<400> SEQUENCE: 57
cgccgctaag tcggtcaccg aacccgacga tgacgcagcc taatag         46

<210> SEQ ID NO 58
<211> LENGTH: 48
<212> TYPE: DNA
<213> ORGANISM: Artificial Sequence
<220> FEATURE:
<223> OTHER INFORMATION: G7R primer

<400> SEQUENCE: 58
ctattaggct gcgtcatcgt cgggttcggt gaccgactta gcggcgat       48

<210> SEQ ID NO 59
<211> LENGTH: 46
<212> TYPE: DNA
<213> ORGANISM: Artificial Sequence
<220> FEATURE:
<223> OTHER INFORMATION: G22F primer

<400> SEQUENCE: 59
cgccgctaag tcggtcaccg aacccgacga tgaggcagcc taatag         46

<210> SEQ ID NO 60
<211> LENGTH: 48
<212> TYPE: DNA
<213> ORGANISM: Artificial Sequence
<220> FEATURE:
<223> OTHER INFORMATION: G22R primer

<400> SEQUENCE: 60
ctattaggct gcctcatcgt cgggttcggt gaccgactta gcggcgat       48

<210> SEQ ID NO 61
<211> LENGTH: 46
<212> TYPE: DNA
<213> ORGANISM: Artificial Sequence
<220> FEATURE:
<223> OTHER INFORMATION: G23F primer

<400> SEQUENCE: 61
cgccgctaag tcggtcaccg aacccgacga tcacgcagcc taatag         46

<210> SEQ ID NO 62
<211> LENGTH: 48
<212> TYPE: DNA
<213> ORGANISM: Artificial Sequence
<220> FEATURE:
<223> OTHER INFORMATION: G23R primer

<400> SEQUENCE: 62
ctattaggct gcgtgatcgt cgggttcggt gaccgactta gcggcgat       48

<210> SEQ ID NO 63
<211> LENGTH: 46
<212> TYPE: DNA
<213> ORGANISM: Artificial Sequence
<220> FEATURE:
<223> OTHER INFORMATION: G29F primer

<400> SEQUENCE: 63
cgccgctaag tcggtcaccg aacccgacga tggcgcagcc taatag         46

<210> SEQ ID NO 64
<211> LENGTH: 48
```

```
<212> TYPE: DNA
<213> ORGANISM: Artificial Sequence
<220> FEATURE:
<223> OTHER INFORMATION: G29R primer

<400> SEQUENCE: 64
ctattaggct gcgccatcgt cgggttcggt gaccgactta gcggcgat        48

<210> SEQ ID NO 65
<211> LENGTH: 46
<212> TYPE: DNA
<213> ORGANISM: Artificial Sequence
<220> FEATURE:
<223> OTHER INFORMATION: G32F primer

<400> SEQUENCE: 65
cgccgctaag tcggtcaccg aacccgacga tttcgcagcc taatag            46

<210> SEQ ID NO 66
<211> LENGTH: 48
<212> TYPE: DNA
<213> ORGANISM: Artificial Sequence
<220> FEATURE:
<223> OTHER INFORMATION: G32R primer

<400> SEQUENCE: 66
ctattaggct gcgaaatcgt cgggttcggt gaccgactta gcggcgat        48

<210> SEQ ID NO 67
<211> LENGTH: 46
<212> TYPE: DNA
<213> ORGANISM: Artificial Sequence
<220> FEATURE:
<223> OTHER INFORMATION: G24F primer

<400> SEQUENCE: 67
cgccgctaag tcggtcaccg aacccgccgc cctggcagcc taatag            46

<210> SEQ ID NO 68
<211> LENGTH: 48
<212> TYPE: DNA
<213> ORGANISM: Artificial Sequence
<220> FEATURE:
<223> OTHER INFORMATION: G24R primer

<400> SEQUENCE: 68
ctattaggct gccagggcgg cgggttcggt gaccgactta gcggcgat        48

<210> SEQ ID NO 69
<211> LENGTH: 46
<212> TYPE: DNA
<213> ORGANISM: Artificial Sequence
<220> FEATURE:
<223> OTHER INFORMATION: G25F primer

<400> SEQUENCE: 69
cgccgctaag tcggtcaccg aacccaagaa gctggcagcc taatag            46

<210> SEQ ID NO 70
<211> LENGTH: 48
<212> TYPE: DNA
<213> ORGANISM: Artificial Sequence
<220> FEATURE:
<223> OTHER INFORMATION: G25R primer

<400> SEQUENCE: 70
ctattaggct gccagcttct tgggttcggt gaccgactta gcggcgat        48
```

<210> SEQ ID NO 71
<211> LENGTH: 46
<212> TYPE: DNA
<213> ORGANISM: Artificial Sequence
<220> FEATURE:
<223> OTHER INFORMATION: G26F primer

<400> SEQUENCE: 71
cgccgctaag tcggtcaccg aaccccgccg cctggcagcc taatag        46

<210> SEQ ID NO 72
<211> LENGTH: 48
<212> TYPE: DNA
<213> ORGANISM: Artificial Sequence
<220> FEATURE:
<223> OTHER INFORMATION: G26R primer

<400> SEQUENCE: 72
ctattaggct gccaggcggc ggggttcggt gaccgactta gcggcgat        48

<210> SEQ ID NO 73
<211> LENGTH: 46
<212> TYPE: DNA
<213> ORGANISM: Artificial Sequence
<220> FEATURE:
<223> OTHER INFORMATION: G9F primer

<400> SEQUENCE: 73
cgccgctaag tcggtcaccg aacccgacga tgacaaggac taatag        46

<210> SEQ ID NO 74
<211> LENGTH: 48
<212> TYPE: DNA
<213> ORGANISM: Artificial Sequence
<220> FEATURE:
<223> OTHER INFORMATION: G9R primer

<400> SEQUENCE: 74
ctattagtcc ttgtcatcgt cgggttcggt gaccgactta gcggcgat        48

<210> SEQ ID NO 75
<211> LENGTH: 55
<212> TYPE: DNA
<213> ORGANISM: Artificial Sequence
<220> FEATURE:
<223> OTHER INFORMATION: MCS linker primer L1

<400> SEQUENCE: 75
taacagctgg cgatcgccag tactggatcc cctgcaggct taagatttaa atgat        55

<210> SEQ ID NO 76
<211> LENGTH: 57
<212> TYPE: DNA
<213> ORGANISM: Artificial Sequence
<220> FEATURE:
<223> OTHER INFORMATION: MCS linker primer L2

<400> SEQUENCE: 76
atcatttaaa tcttaagcct gcaggggatc cagtactggc gatcgccagc tgttaat        57

<210> SEQ ID NO 77
<211> LENGTH: 5
<212> TYPE: PRT
<213> ORGANISM: Mycobacterium tuberculosis

<400> SEQUENCE: 77

```
Asp Asp Leu Ala Ala
1               5

<210> SEQ ID NO 78
<211> LENGTH: 11
<212> TYPE: PRT
<213> ORGANISM: Escherichia coli

<400> SEQUENCE: 78

Ala Ala Asn Asp Glu Asn Tyr Ala Leu Ala Ala
1               5                   10

<210> SEQ ID NO 79
<211> LENGTH: 9
<212> TYPE: PRT
<213> ORGANISM: Mycobacterium tuberculosis

<400> SEQUENCE: 79

Ala Lys Ser Val Thr Glu Pro Asp Asp
1               5

<210> SEQ ID NO 80
<211> LENGTH: 5
<212> TYPE: PRT
<213> ORGANISM: Escherichia coli

<400> SEQUENCE: 80

Trp Val Ala Ala Ala
1               5

<210> SEQ ID NO 81
<211> LENGTH: 5
<212> TYPE: PRT
<213> ORGANISM: Escherichia coli

<400> SEQUENCE: 81

Arg Ser Glu Tyr Glu
1               5

<210> SEQ ID NO 82
<211> LENGTH: 12
<212> TYPE: PRT
<213> ORGANISM: Mycobacterium tuberculosis

<400> SEQUENCE: 82

Ala Lys Ser Val Thr Glu Pro Asp Asp Leu Ala Ala
1               5                   10

<210> SEQ ID NO 83
<211> LENGTH: 12
<212> TYPE: PRT
<213> ORGANISM: Mycobacterium avium

<400> SEQUENCE: 83

Ser Val Ala Arg Arg Thr Gly Gly Glu Leu Ala Ala
1               5                   10
```